Figure 4:
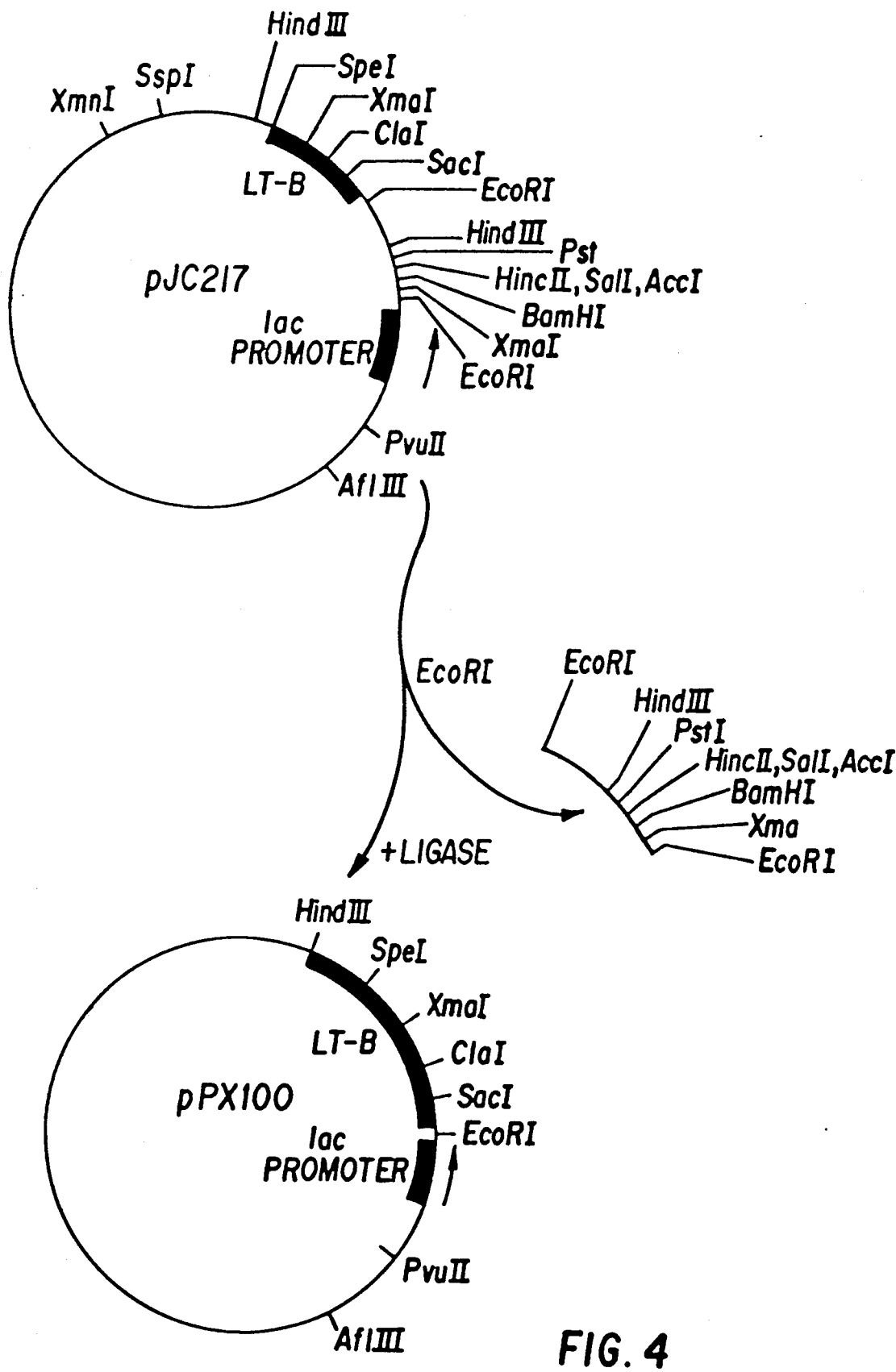

United States Patent [19]

Brey, III et al.

[11] Patent Number: 5,112,749
[45] Date of Patent: May 12, 1992

[54] VACCINES FOR THE MALARIA CIRCUMSPOROZOITE PROTEIN

[75] Inventors: Robert N. Brey, III, Rochester; William R. Majarian, Pittsford; Subramonia Pillai, Rochester; Wayne T. Hockmeyer, Pittsford, all of N.Y.

[73] Assignee: Praxis Biologics, Inc., Rochester, N.Y.

[21] Appl. No.: 104,735

[22] Filed: Oct. 2, 1987

[51] Int. Cl.⁵ .................. C12N 15/00; C12N 1/21; C12N 1/00; C12P 21/02; A01N 63/00; C07H 15/12; C07K 3/00

[52] U.S. Cl. .................... 435/172.3; 435/69.1; 435/257.3; 435/320.1; 435/879; 536/27; 530/350; 935/12; 935/27; 935/41; 935/56; 935/65; 935/72

[58] Field of Search ............... 435/68, 70, 91, 172.1, 435/172.3, 320.1, 879, 69.1, 252.3; 424/88, 93; 530/350; 935/19, 27, 29, 41, 47, 56, 72; 536/27

[56] References Cited

U.S. PATENT DOCUMENTS

| | | | |
|---|---|---|---|
| 4,411,888 | 10/1983 | Klipstein et al. | 424/92 |
| 4,550,081 | 10/1985 | Stocker | 435/253 |
| 4,632,830 | 12/1986 | Formal | 424/92 |
| 4,735,801 | 4/1988 | Stocker | 424/92 |
| 4,751,064 | 6/1988 | Sela et al. | 424/92 |
| 4,758,655 | 7/1988 | Houghton et al. | 530/324 |
| 4,761,372 | 8/1988 | Maas et al. | 435/172.1 |
| 4,837,151 | 6/1989 | Stocker | 435/172.3 |

FOREIGN PATENT DOCUMENTS

| | | |
|---|---|---|
| 0172107 | 2/1986 | European Pat. Off. |
| 249449 | 6/1987 | European Pat. Off. |
| 0357208 | 2/1990 | European Pat. Off. |
| WO86/06635 | 11/1986 | PCT Int'l Appl. |
| 86/00256 | 3/1987 | PCT Int'l Appl. |

OTHER PUBLICATIONS

International Preliminary Examination Report for PCT/US88/00736.
Sadoff et al., *Science*, 240:336-338 (1988).
Romero et al., *Nature* 341:323-325 (Sep. 28, 1989).
Aggarwal et al., *J. Exp. Med.* 172:1083-1090 (1990).
Weiss et al., *J. Exp. Med.* 171:763-773 (1990).
Eichinger, D. et al., Mol and Cell Biol., vol. 6, pp. 3965-3972 (1986).
Arnot, D. et al., Science, vol. 230, pp. 815-818 (1985).
Dame, J. et al., Science, vol. 225, pp. 593-599 (1984).
Clements et al., Inf. Immun., vol. 46, pp. 564-569 (1984).
Perlman, Nature 328: 205-206 (1987).
Ravetch et al., Biotechnology 3: 729-740 (1985).
Miller et al., *Phil. Trans. R. Soc. Lond.* 307: 99-115 (1984).
Levine, et al., *Microbiol.* Rev. 47: 510-550 (1983).
Germanier In Bacterial Vaccines, 137-165, Academic Press, New York (1986).
Hoffman et al., *Science* 237: 639-642 (1987).
Herrington et al., *Nature* 328: 257-259 (1987).
Ballou et al., *The Lancet*, 1277-1281, Jun. 6, 1987.

(List continued on next page.)

*Primary Examiner*—Joan Ellis
*Attorney, Agent, or Firm*—Hamilton, Brook, Smith & Reynolds

[57] ABSTRACT

The present invention is directed to attenuated strains of enteroinvasive bacteria that express a peptide or protein related to an epitope of the malaria parasites of the genus Plasmodium. The bacterial strains of the invention which can multiply in a host without causing significant disease or disorder, and which express a Plasmodium-related peptide that induces a protective immune response against malaria, can be used in live vaccine formulations for malaria. In specific embodiments, a Plasmodium-related peptide can be expressed as a fusion protein, for example, with a bacterial enterotoxin.

The invention also relates to methods for expression of malaria antigens or fragments thereof within attenuated enteroinvasive bacteria.

In particular embodiments, the invention is directed to the expression by attenuated Salmonella spp. of epitopes of Plasmodium circumsporozoite proteins.

50 Claims, 17 Drawing Sheets

OTHER PUBLICATIONS

Young et al., Science 228: 958-962 (1985).
Clements et al., *Infect. Immun.* 53: 685-692 (1986).
Formal et al., *Infect. Immun.* 34: 756-750 (1981).
Maskell, et al., *Microbial Pathogen.* 2: 211-221 (1987).
Brown, et al., *J. Infect. Dis.* 155: 86-92 (1987).
Klipstein et al., *Infect. and Immun.* 44: 268-273 (1984).
Hone et al., *J. Infect. Disc.* 156: 167-174 (1987).
International Search Report.
Guerin-Marchand et al., "A liver-stage-specific antigen of *Plasmodium falciparum* characterized by gene cloning", Sep. 10, 1987, Nature, vol. 329, pp. 164-167.
Ozaki et al., "Plaque antibody selection: rapid immunological analysis of a large number of recombinant phage clones positive to sera raised against *Plasmodium falciparum* antigens", (1986), pp. 213-219, *Journal of Immunological Methods*, 89.
Scaife et al., "Antigens of *Plasmodium falciparum* blood stages with clinical interest cloned and expressed in *E. coli*,", (1986) pp. S119-S137, *Parasitology*, 91.
Stahl et al., "Differential antibody screening of cloned *Plasmodium falciparum* sequences expressed in *Escherichia coli*: Procedure for isolation of defined antigens and analysis of human antisera", Apr. 1984, pp. 2456-2460, *Proc. Natl. Acad. Sci. USA*, vol. 88.
McGarvey et al., "Identification and expression in *Escherichia coli* of merozoite stage-specific genes of the human malarial parasite *Plasmodium falciparum*", pp. 3690-3694, vol. 81, Jun. 1984, *Proc. Natl. Acad. Sci. USA*.
Zavala et al., Science, vol. 228, pp. 1436-1440 (1985).
Ellis et al., Nature, vol. 302, pp. 536-538 (1983).

```
         Toq I          Nru I          Hinc II
        AATTCGAAC  CCCTTCGCGA  AATACAGTCA  ACAGATTACT  TGCCGATGCT  CCCGAAGGAA
            Xmn I              └──▶CS gene sequence

AAAAAAATGA  GAAAAAAAAC  GAAAAAATAG  AGCGTAATAA  TAAATTGAAA  CAACCACCAC

CACCACCAAA  CCCAAATGAC  CCACCACCAC  CAAACCCAAA  TGACCCACCA  CCACCAAACC

CAAATGACCC  ACCACCACCA  AACGCAAATG  ACCCAGCACC  ACCAAACGCA  AATGACCCAG

CACCACCAAA  CGCAAATGAC  CCAGCACCAC  CAAACGCAAA  TGACCCAGCA  CCACCAAACG

CAAATGACCC  AGCACCACCA  AACGCAAATG  ACCCAGCACC  ACCAAACGCA  AATGACCCAG

CACCACCAAA  CGCAAATGAC  CCACCACCAC  CAAACCCAAA  TGACCCAGCA  CCACCACAAG

GAAATAACAA  TCCACAACCA  CAGCCACGGC  CGCAGCCACA  ACCACAGCCA  CAGCCACAAC

CACAGCCACA  GCCACAACCA  CAGCCACGAC  CACAGCCACA  ACCACAGCCA  GGTGGTAATA

ACAATAACAA  AAATAATAAT  AATGACGATT  CTTATATCCC  AAGCGCGGAA  AAAATACTAG

AATTTGTTAA  ACAGATCAGG  GATAGTATCA  CAGAGGAATG  GTCTCAATGT  AACGTAACAT
                                  Xmn I
GTGGTTCTGG  TATAAGAGTT  AGAAAACGAA  AAGGTTCAAA  TAAGAAAGCA  GAAGATTTGA
                                                                   SspI
CCTTAGAAGA  TATTGATACT  GAAATTTGTA  AAATGGATAA  ATGTTCAAGT  ATATTTAATA
                    SspI
TTGTAAGCAA  TTCATTAGGA  TTTGTAATAT  TATTAGTATT  AGTATTCTTT  AATTAAATAA
                   SspI                        SspI
ACATTACGCA  TGATTATAAA  TATTTATATA  TTATATAAAT  ATTTTACATA  CATATGACGT

GTGTAAACTT  TATTTTTTTT  ATTGTGAACT  TTTCCTTATT  TATTACGATT  ATGTTTATAT

GTATATATAT  TTAATATGTA  AATCAAAAGA  AAAAATAAAT  AATAGAAGGC  TTATTATATT

TATAATATAA  ATTAAAAAAT  AAAATATATA  TGCATTACAA  AATTTACTTT  TTTTAGTTTA
                                                        XmnI
TTTTTTTCGT  GTTTATTATA  TATGTAGTTA  ACTTGCTATG  ACGATATCGC  GAAGGGGTTC
                                                        NruI      ToqI
GAATT
```

FIG. 1

```
CGA AAT ACA GTC AAC AGA TTA CTT GCC GAT GCT CCC GAA GGA AAA AAA AAT GAG AAA AAA
Arg Asn Thr Val Asn Arg Leu Leu Ala Asp Ala Pro Glu Gly Lys Lys Asn Glu Lys Lys

AAC GAA AAA ATA GAG CGT AAT AAT AAA TTG AAA CAA CCA CCA CCA CCA CCA AAC CCA AAT
Asn Glu Lys Ile Glu Arg Asn Asn Lys Leu Lys Gln Pro Pro Pro Pro Pro Asn Pro Asn
                                      └──── Region I ────┘

[GAC CCA CCA CCA CCA AAC CCA AAT][GAC CCA CCA CCA CCA AAC CCA AAT][GAC CCA CCA CCA
[Asp Pro Pro Pro Pro Asn Pro Asn][Asp Pro Pro Pro Pro Asn Pro Asn][Asp Pro Pro Pro

CCA AAC GCA AAT][GAC CCA GCA CCA CCA AAC GCA AAT][GAC CCA GCA CCA CCA AAC GCA AAT]
Pro Asn Ala Asn][Asp PRo Ala Pro Pro Asn Ala Asn][Asp Pro Ala Pro Pro Asn Ala Asn]

[GAC CCA GCA CCA CCA AAC GCA AAT][GAC CCA GCA CCA CCA AAC GCA AAT][GAC CCA GCA CCA
[Asp Pro Ala Pro Pro Asn Ala Asn][Asp Pro Ala Pro Pro Asn Ala Asn][Asp Pro Ala Pro

GCA AAC GCA AAT][GAC CCA GCA CCA CCA AAC GCA AAT][GAC CCA GCA CCA CCA AAC GCA AAT]
Pro Asn Ala Asn][Asp Pro Ala Pro Pro Asn Ala Asn][Asp Pro Ala Pro Pro Asn Ala Asn]

GAC CCA CCA CCA CCA AAC CCA AAT GAC CCA GCA CCA CCA CAA GGA AAT AAC AAT [CCA CAA]
Asp Pro Pro Pro Pro Asn Pro Asn Asp Pro Ala Pro Pro Gln Gly Asn Asn Asn [Pro Gln]

[CCA CAG][CCA CGG][CCG CAG][CCA CAA][CCA CAG][CCA CAG][CCA GAA][CCA CAG][CCA CAG][CCA CAA]
[Pro Gln][Pro Arg][Pro Gln][Pro Gln][Pro Gln][Pro Gln][Pro Glu][Pro Gln][Pro Gln][Pro Gln]

CCA CAG CCA CGA CCA CAG CCA CAA CCA CAG CCA GGT GGT AAT AAC AAT AAC AAA AAT AAT
Pro Gln Pro Arg Pro Gln Pro Gln Pro Gln Pro Gly Gly Asn Asn Asn Asn Lys Asn Asn

AAT AAT GAC GAT TCT TAT ATC CCA AGC GCG GAA AAA ATA GTA GAA TTT GTT AAA CAG ATC
Asn Asn Asp Asp Ser Tyr Ile Pro Ser Ala Glu Lys Ile Leu Glu Phe Val Lys Gln Ile

AGG GAT AGT ATC ACA GAG GAA TGG TCT CAA TGT AAC GTA ACA TGT GGT TCT GGT ATA AGA
Arg Asp Ser Ile Thr Glu Glu Trp Ser Gln Cys Asn Val Thr Cys Gly Ser Gly Ile Arg
             └──── Region II ────┘

GTT AGA AAA CGA AAA GGT TCA AAT AAG AAA GCA GAA GAT TTG ACC TTA GAA GAT ATT GAT
Val Arg Lys Arg Lys Gly Ser Asn Lys Lys Ala Glu Asp Leu Thr Leu Glu Asp Ile Asp

ACT GAA ATT TGT AAA ATG GAT AAA TGT TCA AGT ATA TTT AAT ATT GTA AGC AAT TCA TTA
Thr Glu Ile Cys Lys Met Asp Lys Cys Ser Ser Ile Phe Asn Ile Val Ser Asn Ser Leu

GGA TTT GTA ATA TTA TTA GTA TTA GTA TTC TTT AAT TAA ATA AAC ATT ACG CAT GAT TAT
Gly Phe Val Ile Leu Leu Val Leu Val Phe Phe Asn

AGA TAT TTA TAT ATT ATA TAA ATA TTT TAC ATA CAT ATG ACG TGT GTA AAC TTT ATT TTT
```

FIG.2

```
 EcoRI             ┌─ SIGNAL SEQUENCE
AAT TCG GGA TGA ATT ATG AAT AAA GTA AAA TTT TAT GTT TTA TTT ACG GCG TTA CTA TCC
     └─┬─┘          Met Asn Lys Val Lys Phe Tyr Val Leu Phe Thr Ala Leu Leu Ser
      S/D        SacI ┌─Mature LT-B
TCT CTA TGT GCA CAC GGA GCT CCT CAG TCT ATT ALA GAA CTA TGT TCG GAA TAT CAC AAC
Ser Leu Cys Ala His Gly Ala Pro Gln Ser Ile Thr Glu Leu Cys Ser Glu Tyr His Asn
                                                               Cla I
ACA CAA ATA TAT ACG ATA AAT GAC AAG ATA CTA TCA TAT ACG GAA TCG ATG GCA GGC AAA
Thr Gln Ile Tyr Thr Ile Asn Asp Lys Ile Leu Ser Tyr Thr Glu Ser Met Ala Gly Lys
                                                                      Xma I
AGA GAA ATG GTT ATC ATT ACA TTT AAG AGC GGC GCA ACA TTT CAG GTC GAA GTC CCG GGC
Arg Glu Met Val Ile Ile Thr Phe Lys Ser Gly Ala Thr Phe Gln Val Glu Val Pro Gly AGT CAA CAT ATA GAC TCC CAA AAA AAA GCC ATT GAA AGG ATG AAG GAC ACA TTA AGA ATC
Ser Gln His Ile Asp Ser Gln Lys Lys Ala Ile Glu Arg Met Lys Asp Thr Leu Arg Ile ACA TAT CTG ACC GAG ACC AAA ATT GAT AAA TTA TGT GTA TGG AAT AAT AAA ACC CCC AAT
Thr Tyr Leu Thr Glu Thr Lys Ile Asp Lys Leu Cys Val Trp Asn Asn Lys Thr Pro Asn
                                       Spe I
TCA ATT GCG GCA ATC AGT ATG GAA AAC TAG TTT GCT TTA AAA GCA TGT CTA ATG CTA GGA
Ser Ile Ala Ala Ile Ser Met Glu Asn

ACC TAT ATA ACA ACT ACT GTA CTT ATA CTA ATG AGC CTT ATG CTG CAT TTG AAA AGG CGG

TAG AGG ATG CAA TAC CGA TCC TTA AAC TGT AAC ACT ATA ACA GCT TCC ACT ACA GGG AGC
                                                             Hind III
TGT TAT AGC AAA CAG AAA AAA CTA AGC TAG GCT GGG GGG GCA AGC TT
```

- TY523
- pPX1532/TY532
- pPX1532/JM103 −IPTG
- pPX1532/JM103 +IPTG

SL1438
2/SL1438
SL3261
2/L3261

VACCINES FOR THE MALARIA CIRCUMSPOROZOITE PROTEIN

1. FIELD OF THE INVENTION

The present invention is directed to attenuated strains of enteroinvasive bacteria that express peptides and proteins related to epitopes of the malaria parasites of the genus Plasmodium. The bacterial strains of the present invention which can multiply in a host without causing significant disease or disorder, and which express Plasmodium-related peptides that induce a protective immune response against malaria, can be used in live vaccine formulations for malaria. Such vaccine formulations can be univalent or multivalent.

In particular, the vaccine vector strains of the present invention comprise attenuated Salmonella bacteria which retain their enteroinvasive properties but lose in large part their virulence properties.

In a preferred embodiment of the invention, a gene or gene fragment encoding all or part of the circumsporozoite malaria antigen can be expressed in Salmonella bacteria that have been attenuated by chromosomal deletion of gene(s) for aromatic compound biosynthesis, for use as a live vaccine for malaria.

2. BACKGROUND OF THE INVENTION

2.1. RECOMBINANT DNA TECHNOLOGY AND GENE EXPRESSION

Recombinant DNA technology involves insertion of specific DNA sequences into a DNA vehicle (vector) to form a recombinant DNA molecule which is capable of replication in a host cell. Generally, the inserted DNA sequence is foreign to the recipient DNA vehicle, i.e., the inserted DNA sequence and the DNA vector are derived from organisms which do not exchange genetic information in nature, or the inserted DNA sequence may be wholly or partially synthetically made. Several general methods have been developed which enable construction of recombinant DNA molecules.

Regardless of the method used for construction, the recombinant DNA molecule must be compatible with the host cell, i.e., capable of autonomous replication in the host cell or stably integrated into one or more of the host cell's chromosomes. The recombinant DNA molecule should preferably also have a marker function which allows the selection of the desired recombinant DNA molecule(s). In addition, if all of the proper replication, transcription, and translation signals are correctly arranged on the recombinant vector, the foreign gene will be properly expressed in, e.g., the transformed bacterial cells, in the case of bacterial expression plasmids, or in permissive cell lines or hosts infected with a recombinant virus or carrying a recombinant plasmid having the appropriate origin of replication.

Different genetic signals and processing events control levels of gene expression such as DNA transcription and messenger RNA (mRNA) translation. Transcription of DNA is dependent upon the presence of a promoter, which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and furthermore, procaryotic promoters are not recognized and do not function in eucaryotic cells.

Similarly, translation of mRNA in procaryotes depends upon the presence of the proper procaryotic signals, which differ from those of eucaryotes. Efficient translation of mRNA in procaryotes requires a ribosome binding site called the Shine-Dalgarno (S/D) sequence (Shine, J. and Dalgarno, L., 1975, Nature 254:34-38) on the mRNA. This sequence is a short nucleotide sequence of mRNA that is located before the start codon, usually AUG, which encodes the amino-terminal methionine of the protein. The S/D sequences are complementary to the 3' end of the 16S rRNA (ribosomal RNA), and probably promote binding of mRNA to ribosomes by duplexing with the rRNA to allow correct positioning of the ribosome (id.).

Successful expression of a cloned gene requires sufficient transcription of DNA, translation of the mRNA and in some instances, post-translational modification of the protein. Expression vectors have been used to express genes under the control of an active promoter in a suitable host, and to increase protein production.

2.2. VACCINATION AGAINST MALARIA

A global public health goal is the control and eventual eradication of human malaria. It is estimated that over 500 million people in tropical regions are exposed to malaria annually, and 1.5 to 2 million people die from this disease (Sturchler, D., 1984, Experientia 40:1357). Efforts to control malaria have historically focussed on control of the mosquito vector and the development of antimalarial drugs. These efforts have met with only limited success. New prophylactic and therapeutic drugs are of limited effectiveness because drug-resistant strains can appear rapidly in endemic areas. Control of the mosquito vector depends largely upon implementation of insecticide-based control programs which, due to cost and other factors, are difficult to maintain in developing nations. Vector resistance to modern insecticides has compounded the problem, and resulted once again in the resurgence of malaria.

Mammalian hosts can be infected by the sporozoite form of the malaria parasite, which is injected by the female Anopheles mosquito during feeding. Sporozoites injected into the bloodstream are carried rapidly to the liver where they invade hepatocytes. Once in hepatocytes, sporozoites develop into merozoite forms, which are released from hepatocytes and invade erythrocytes. Within the erythrocyte, the parasite asexually reproduces, from rings to schizonts. The mature schizont contains merozoites which, upon rupture of the erythrocyte, can invade other erythrocytes, causing clinical manifestations of the disease. Some merozoites differentiate into sexual forms, called gametocytes, which are taken up by mosquitoes during a blood meal. After fertilization of gametocytes in the mosquito midgut, developing ookinetes can penetrate the gut wall and encyst. Rupture of such oocysts allows release of sporozoites which migrate to the salivary glands to be injected when the female mosquito takes another blood meal, thus completing the infectious cycle.

Experiments conducted in the 1960s demonstrated that vaccination with X-irradiated sporozoites of *P. berghei* protected mice against sporozoite challenge which was lethal in unvaccinated animals (Nussenzweig, R., et al., 1969, Mil. Med. 134:1176). This observation was later extended to clinical studies in humans, where immunization with X-irradiated sporozoites of *P.*

*falciparum* or *P. vivax* protected human volunteers against sporozoite challenge delivered through the bites of infected mosquitoes (Clyde, D. F., et al., 1975, Am. J. Trop. Med. Hyg. 24:397; Rieckmann, K. H., et al., 1979, Bull. WHO 57:261). This protection was thought to be mediated by antibody. Serum from immunized animals, including humans, formed a precipitate around the surface of live, mature sporozoites. This reaction has been termed the circumsporozoite precipitin (CSP) reaction. These same sera blocked the ability of sporozoites to invade human hepatoma cells in culture (ISI assay) (Hollingdale, M. R., et al., 1984, J. Immunol. 132:909). In other studies, a single antigenic determinant localized on the surface of *P. berghei* sporozoites, termed the circumsporozoite protein, was identified. It was shown that a monoclonal antibody reacting with the circumsporozoite (CS) protein of *P. berghei* could passively transfer immunity to recipient animals. These animals were protected from sporozoite challenge in a dose-dependent fashion (Potocnjak, P. N., et al., 1980, J. Exp. Med. 151:1504). Evidence also existed that cell-mediated immunity was important (Chen, D. H., et al., 1977, J. Immunol. 118:1322; Verhave, J. P., et al., 1978, J. Immunol 121:1031).

The first CS protein gene to be cloned was derived from the H strain of *P. knowlesi*, a simian parasite (Ozaki et al., 1983, Cell 34:815). The genes encoding the CS proteins of the human malaria parasites *P. falciparum* (Dame et al., 1984, Science 225:593), *P. vivax* (McCutchan et al., 1984, Science 230:1381), the simian parasite *P. cynomolgi* (Enea et al., 1984, Science 225:628), and the rodent parasite *P. berghei* (Weber et al., 1987, Exp. Parasitol. 63:295) were also cloned and sequenced. A characteristic feature of the CS genes of each of the parasites is a central region which encodes over one-third of the protein, containing a series of repeated peptide sequences. The primary amino acid sequence, the length of the repeated sequence, and the number of repeats vary with each species of parasite. The repeat region epitopes are characteristic of each species. The gene encoding the CS protein of *P. falciparum* specifies a central repeat region of a tetrapeptide (asn-ala-asn-pro) repeated 37 times, interrupted in four locations by the nonidentical tetrapeptide (asn-val-asp-pro). The central repeat region of *P. vivax* CS protein contains 19 nonapeptides; the central sequence of *P. knowlesi* contains 12 dodecapeptides, and the repeat region of *P. berghei* contains 12 octapeptides. Comparison of sequences from *P. knowlesi* (H strain) and *P. falciparum* and *P. vivax* reveals no sequence homology except for two short amino acid sequences flanking the repeat region, termed Region I and Region II.

Efforts to develop an effective anti-sporozoite vaccine for *P. falciparum* have used peptides derived from the circumsporozoite (CS) repeat region and the two flanking Region I and Region II sequences (Ballou, W. R., et al., 1985, Science 228:996). These experiments showed that antibody to the repeat region but not to the conserved sequences recognized authentic CS protein, produced CSP activity, and blocked sporozoite invasion (ISI) in vitro. A recombinant DNA subunit vaccine composed of 32 *P. falciparum* tetrapeptide repeats fused to 32 amino acids of the tetracycline resistance gene was produced in *E. coli* (Young, J. F., et al., 1985, Science 228:958) Likewise, a peptide-carrier vaccine composed of three repeats of the peptide asn-ala-asn-pro (NANP) conjugated to tetanus toxoid was developed (Zavala, F., et al., 1985, Science 228:1436). In each case, preclinical studies indicated that biologically active (as shown by CSP and ISI) anti-sporozoite antibodies were elicited as a result of immunization (Ballou, R., et al., 1987, The Lancet 1:1277; Herrington et al., 1987, Nature 328:257). Human safety and immunogenicity studies with both vaccines yielded similar results. Both vaccine preparations were well tolerated at doses ranging from 10 micrograms to 800 micrograms, and both elicited some anti-CS antibodies in all immunized subjects. However, high titers were not achieved. In addition, subsequent booster immunizations with the peptide-carrier vaccine did not result in increased antibody titers. Several individuals from each study were then challenged with live sporozoites in order to test the efficacy of these vaccine preparations. Once again, similar results were achieved with both vaccines; the level of protection (as measured by a delay in the appearance of blood stage parasites) correlated with the anti-CS antibody titers of the challenged individuals, but in each trial, only one individual was protected. Parallel studies to evaluate the feasibility of human subunit vaccine development have been examined in the rodent *P. berghei* malaria model (Egan et al., 1987, Science 236:453).

A recent study has reported that levels of naturally acquired antibodies to the *P. falciparum* CS protein, as high as those achieved by a subunit sporozoite vaccine (Ballou, W. R., et al., 1987, Lancet 1987-I:1277), did not protect against *P. falciparum* infection during a 98-day interval in a malaria-endemic area.

In different studies, subunit vaccines containing peptides of other *P. falciparum* antigens have been investigated (Patarroyo, M. E., et al., 1987, Nature 629-632; Cheung, A., et al., 1986, Proc. Natl. Acad. Sci. U.S.A. 83:8328-8332; Collins, W. E., et al., 1986, Nature 323 259-262). In addition, recombinant vaccinia viruses which express *P. falciparum* antigens have been described for use (PCT International Publication Number WO 87/01386, published Mar. 12, 1987).

Perspectives and recent advances in malaria vaccination have been described (Miller, L. H., et al., 1984, Phil. Trans. R. Soc. Lond. B307:99-115; 1985, Vaccines87, Channock et al., eds., Cold Spring Harbor Laboratory, Cold Spring Harbor, N.Y. pp. 81-106, 117-124).

2.3. BACTERIA OF THE GENUS SALMONELLA

Bacteria of the genus Salmonella include over 2,000 serotypes, many of which are capable of causing enteric disease in man and animals. Of the diseases most frequently associated with Salmonella outbreak, typhoid fever is notable for its severity and high mortality. In humans, typhoid (or enteric) fever results from invasion and dissemination of *S. typhi*, although other members of the Salmonella are capable of invading and localizing in organ tissues, causing less severe symptoms. In other outbreaks of salmonellosis (such as food poisoning), the disease is non-invasive and confined to symptoms of gastroenteritis, and in humans, the disease is not associated with *S. typhi*. In animals, outbreaks of typhoid fever may be associated with numerous serotypes, e.g., *S. choleraesuis* in swine, *S. gallinarum* in poultry, and *S. dublin* and *S. typhimurium* in cattle (Topley and Wilson's Principles of Bacteriology, Virology, and Immunity, 6th ed., Williams & Wilkins Co., Baltimore, Md.). The host specificity and severity of the resultant disease varies among the serotypes of Salmonella.

The first instance of an attenuated oral vaccine for typhoid fever in humans was a streptomycin-dependent S. typhi, but the use of that strain was discontinued. Germanier (Germanier, R. and Furer, E., 1975, J. Infect. Dis. 131:553; Germanier, R., 1984 in Bacterial Vaccines, Academic Press, New York, pp. 137–165) advocated the use of a galE mutant of S. typhi as an oral vaccine against human typhoid fever.

The S. typhi galE mutant, Ty21a, is capable of eliciting a protective response against the pathogenic parental strain in human volunteers (Levine, M. M., et al., 1983, Microbiol. Rev. 47:510; Wahdan, M. H., et al., 1982, J. Infect. Dis. 145:292). The Ty21a strain also has yielded promising protective results in a field test with 28,000 school children in Alexandria, Egypt (Wahdan, M. H., et al., 1982, J. Infect. Dis. 145:292). This vaccine strain is being marketed in Europe as a typhoid fever vaccine. However, a major disadvantage of this vaccine strain is that it exhibits variable viability due to killing by exogenous galactose. Addition of galactose has two effects on the Ty21a (galE mutant) strain. Firstly, it results in the accumulation of toxic galactose-1-phosphate, causing reduced viability. Secondly, added galactose is incorporated into the polysaccharide chain of lipopolysaccharide, which is necessary for immunogenicity. These opposing requirements result in variability in viability and in immunogenicity of the vaccine strain.

Recently, Stocker and his coworkers have described a reliable method to achieve attenuation of Salmonella (e.g., Hoiseth and Stocker, 1981, Nature 291:238; Stocker et al., 1982, Develop. Biol. Standard 53:47; and U.S. Pat. No. 4,550,081). In this method, specific deletion mutations affecting the aromatic biosynthetic pathway are introduced by transduction. Specifically, deletions of the gene aroA result in pleiotropic requirements for phenylalanine, tryptophan, tyrosine, and the folic acid precursor, p-aminobenzoic acid, and the enterochelin precursor, dihydroxybenzoic acid. The aromatic amino acids are present in animal tissues, but p-aminobenzoic acid is absent; folic acid which may be present in animal cells is not assimilated by members of the Enterobacteriaceae. In addition, absence of enterochelin results in the requirement for iron in aroA Salmonella strains.

Since the introduction of techniques for the precise attenuation of Salmonella, a number of vaccination studies have been undertaken in animal model systems (Lindberg, A. A. and Robertsson, J. A., 1983, Infect. Immun. 41:751; Robertsson, J. A., et al., 1983, Infect. Immun. 41:742; Smith, B. P., et al., 1984, Am. J. Vet. Res. 45:2231; Smith, B. P., et al., 1984, Am. J. Vet. Res. 45:59; Stocker, B. A. D., et al., 1982, Develop. Biol. Standard 53:47). Using an aroA derivative of S. typhimurium UCD 108-11, SL1479, in the calf model system, Lindberg and coworkers demonstrated invasiveness of SL1479, and showed that calves vaccinated with SL1479 cleared the vaccine organism quickly from the gut and tissues Oral vaccination with live SL1479 gave greater protection and cell-mediated immune reactivity against S. typhimurium UCD 108-11 infection than that obtained by intraperitoneal vaccination with heat-killed organisms. In other studies, Smith and colleagues demonstrated protection in calves by vaccination with SL1479, against challenge by the virulent parental strain.

A number of groups have demonstrated expression of heterologous genes in Salmonella. Formal and colleagues transferred the genes for the form I antigen of Shigella sonnei into Salmonella typhi Ty21a (see e.g., Formal, S. B., et al., 1981, Infect. Immun. 34:746; Tramont et al., 1984, J. Inf. Dis. 149:133; and U.S. Pat. No. 4,632,830, by Formal et al.). The form I antigen of Shigella is associated with immunity elicited by vaccination with live attenuated Shigella sonnei. Subcutaneous or intraperitoneal injection of living transconjugants protected mice against intraperitoneal challenge by either S. typhi Ty21a or Shigella sonnei. Also, by conjugation experiments, Yamamoto and coworkers (Yamamoto, T., et al., 1982, J. Bacteriol. 150:1482) introduced an E. coli colonization factor antigen (CFA/I) into Salmonella typhi Ty21a and demonstrated expression of the antigen.

Clements et al. (1983, Infect. Immun. 53:685) tested antibody responses to the B subunit of heat labile toxin (LT-B), derived from enteroinvasive E. coli (EIEC) of human origin (Strain H10407), expressed on a recombinant plasmid in S. typhi Ty21a. Since S. typhi has a host range limited to humans and higher primates, immunogenicity was tested in an animal model. Intraperitoneal injection of the heterologous LT-B in Ty21a resulted in serum antibody responses to LT-B in mice (Clements, J. D. and S. El-Morshidy, 1984, Infect. Immun. 46:564). Subsequently, LT-B producing recombinants were examined in an attenuated Salmonella strain infectious for mice (Clements, J. D., et al., 1986, Infect. Immun. 53:685). In this study, the LT-B gene was introduced into an aroA attenuated S. enteriditis serotype dublin strain: SL1438. The parental S. enteriditis dublin strain is virulent in BALB/c mice. After oral vaccination with the recombinant Salmonella strain, EL23, a significant increase in mucosal anti-LT-B IgA was observed. The response to LT-B produced by the recombinant organism was less marked than the immune response to purified LT-B injected intraperitoneally or given orally (id.).

In another study, after introduction of LT-B-encoding plasmids into a aroA deletion mutant of S. typhimurium, SL3261, oral or intraperitoneal vaccination with the recombinant bacteria in mice induced an antibody response to LT-B (Maskell et al., 1987, Microbial Pathogenesis 2:211).

Several other groups have also reported expression of heterologous antigens in attenuated Salmonella. Manning and coworkers (Manning, P. A., et al., 1986, Infect. Immun. 53:272) have cloned the gene clusters responsible for lipopolysaccharide synthesis of the O antigens of the major biotypes of Vibrio cholerae: Inaba and Ogawa. These gene clusters were expressed on the surface of S. typhi Ty21a. The K88 fimbrial adhesin antigen of Escherichia coli strains associated with diarrhea of neonatal piglets has been cloned and expressed in S. typhimurium SL3261 (Dougan et al., 1986, Infect. Immun. 52:344). Antibodies against the K88 antigen were obtained from sera of mice receiving either oral or intravenous doses of the recombinant S. typhimurium. In addition, beta-galactosidase has been expressed in S. typhimurium SL3261, and specific anti-beta-galactosidase antibodies were elicited by administration of the recombinant bacteria to mice (Brown, A., et al., 1987, J. Inf. Dis. 155:86), demonstrating that the intracellular beta-galactosidase protein can also provoke an immune response.

3. SUMMARY OF THE INVENTION

The present invention is directed to attenuated strains of enteroinvasive bacteria that express peptides and proteins related to epitopes of the malaria parasites of the genus Plasmodium. The bacterial strains of the invention which can multiply in a host without causing significant disease or disorder, and which express Plasmodium-related peptides that induce a protective immune response against malaria, can be used in live vaccine formulations for malaria. Such vaccine formulations can be univalent or multivalent.

The expression of Plasmodium epitopes in attenuated enteroinvasive bacteria in the vaccine formulations of the invention provides protective immunity against malaria due to the ability to evoke a cell-mediated immune response in addition to a humoral response. Cell-mediated immunity directed against the Plasmodium epitope results from the invasive properties of the bacteria, which allow presentation of the epitope to the immune system in a manner which can induce cell-mediated immunity.

In particular, the vaccine vector strains of the present invention comprise attenuated Salmonella bacteria which retain their enteroinvasive properties but lose in large part their virulence properties. By obtaining expression of a malarial epitope in attenuated Salmonella, the epitope can be effectively presented to cells important in immune recognition by bacterial invasion, without bacterial persistence or virulence. Thus, effective vaccines against malaria can be achieved. In a preferred embodiment of the invention, a gene or gene fragment encoding all or part of the circumsporozoite malaria antigen can be expressed in Salmonella bacteria that have been attenuated by chromosomal deletion of gene(s) for aromatic compound biosynthesis, for use as a live vaccine for malaria.

The present invention also relates to the methods for expression of the malaria proteins or fragments thereof within attenuated enteroinvasive bacteria. The invention demonstrates the use of plasmid vectors designed for malaria peptide or protein expression in attenuated enteroinvasive bacteria. In particular embodiments, the invention is directed to methods of obtaining expression of circumsporozoite proteins in attenuated Salmonella spp., and relates to DNA sequences encoding the circumsporozoite proteins of *P. falciparum, P. vivax, P. ovale, P. malariae, P. berghei, P. yoelii, P. knowlesi,* and *P. cynomolgi*. The circumsporozoite proteins of the above species of Plasmodium can be expressed in an attenuated Salmonella strain which is enteroinvasive in the animal host for the appropriate malaria parasite.

In another embodiment, the invention relates to the expression, by attenuated enteroinvasive bacteria, of malaria proteins as recombinant fusion proteins. For example, DNA encoding the circumsporozoite protein or an epitope thereof can be joined to the gene for the B subunit of the heat-labile enterotoxin of *E. coli* (LT-B), or a portion thereof, in order to achieve enhanced immunogenicity.

In specific embodiments of the present invention described in the examples sections herein, the construction of recombinant plasmid expression vectors which encode epitopes of the circumsporozoite protein of *P. berghei*, or of *P. falciparum*, are described. The expression of recombinant LT-B/CS fusion proteins in attenuated Salmonella strains is demonstrated. The recombinant Salmonella which express CS peptides are shown to elicit anti-CS antibody production in mice, and to provoke immune responses which protect against malaria infection upon sporozoite challenge.

3.1. DEFINITIONS

| | | |
|---|---|---|
| CS | = | circumsporozoite |
| CSP reaction | = | circumsporozoite precipitin reaction |
| DNase | = | deoxyribonuclease |
| DTT | = | dithiothreitol |
| EIEC | = | enteroinvasive *E. coli* |
| ELISA | = | enzyme-linked immunoabsorbent assay |
| i.p. | = | intraperitoneally |
| IPTG | = | isopropylthio-beta-D-galactoside |
| ISI | = | inhibition of sporozoite invasion |
| kD | = | kiloDalton |
| KLH | = | keyhole limpet hemocyanin |
| LB | = | Luria broth |
| LT-B | = | the B subunit of the heat-labile enterotoxin of *E. coli* |
| mAb | = | monoclonal antibody |
| PAGE | = | polyacrylamide gel electrophoresis |
| PBS | = | phosphate-buffered saline |
| $P_L$ | = | leftward promoter of bacteriophage lambda |
| $P_R$ | = | rightward promoter of bacteriophage lambda |
| RNase | = | ribonuclease |
| S/D | = | Shine-Dalgarno |
| SDS | = | sodium dodecyl sulfate |

4. BRIEF DESCRIPTION OF THE FIGURES

FIG. 1. Nucleotide sequence of the *P. berghei* circumsporozoite gene. Sequence data is according to Weber et al., 1987, Experimental Parasitol. 63:295. The gene sequence comprises approximately 75% of the sequence of the mature gene and includes the sequence of linkers used in the original cloning of the gene in lambda gt11. Major restriction enzyme sites are indicated. The *P. berghei* specific DNA starts with the CGA codon encompassing the first NruI site.

FIG. 2. Nucleotide and amino acid sequence of the *P. berghei* circumsporozoite protein. The repeated immunodominant epitopes are shown in brackets, and consist of a consensus octapeptide repeat, DPAPPNAN, and a second less frequent octapeptide repeat, DPPPPNPN. Regions I and II are underlined. Repeated dipeptide units are also shown in brackets.

FIG. 3. Gene and protein sequence of LT-B derived from *Escherichia coli* H10407. The DNA sequence and protein sequence of the coding region of the LT-B gene is included within a 588 base pair EcoRI-HindIII restriction fragment. A short Shine-Dalgarno site is within seven base pairs of the initiating codon ATG, and is underlined. The protein sequence of LT-B includes a 21 amino acid signal sequence (shown in brackets) which is processed in the mature form, beginning with alanine. The ClaI, XmaI, and SpeI restriction enzyme recognition sites in LT-B which were useful in constructing fusion protein molecules are shown.

FIG. 4. Is a diagrammatic representation of the construction of plasmid pPX100, a vector which expresses LT-B under the control of the lac operon. Plasmid pJC217 was digested with EcoRI and religated to delete 180 base pairs of DNA including extraneous restriction sites of the polylinker, to yield plasmid pPX100.

Figure 5:
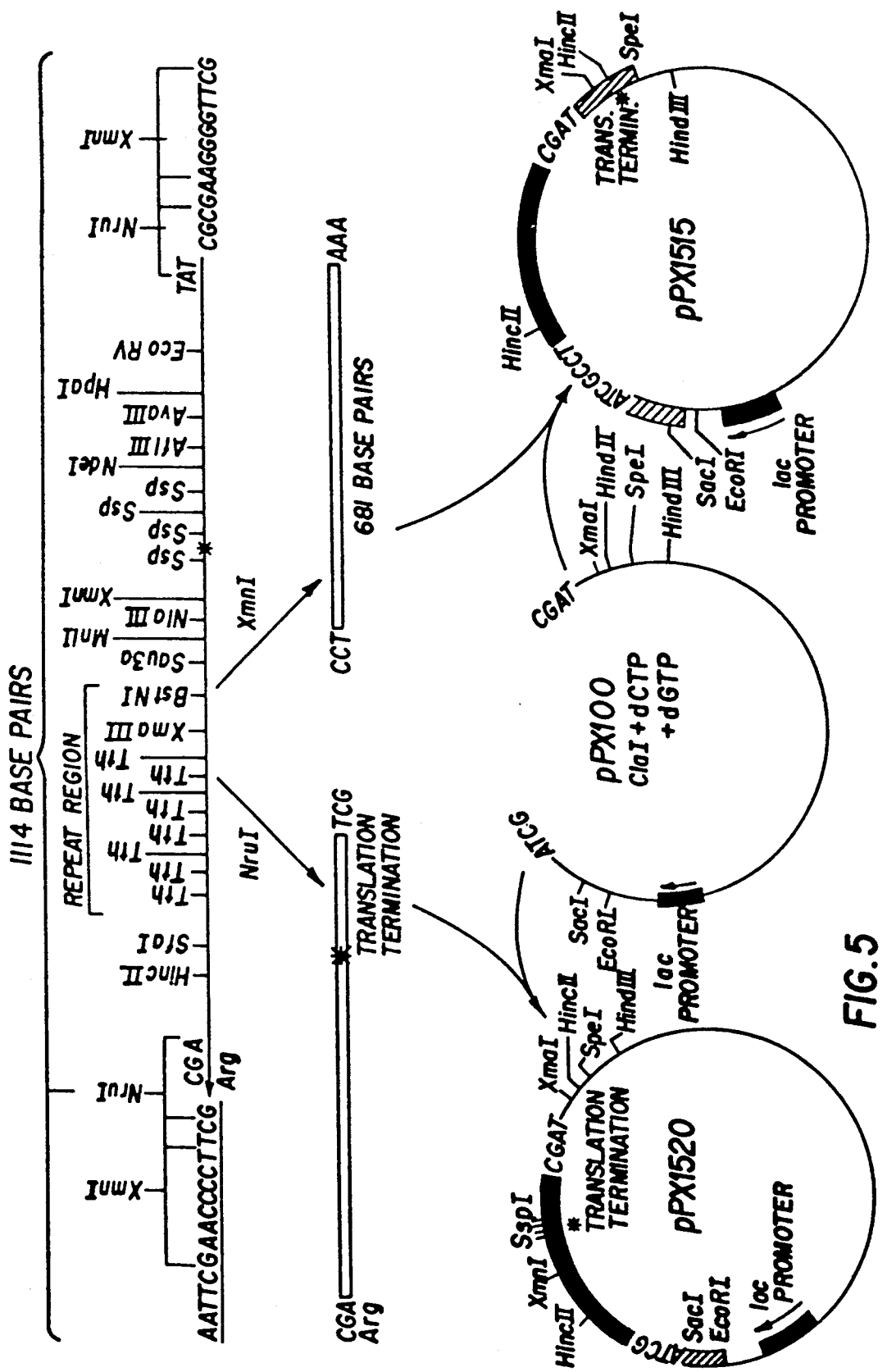

FIG. 5. Is a diagrammatic representation of the construction of plasmid vectors which express LT-B/CS fusion proteins under the control of the lac operon. The DNA sequence of the *P. berghei* CS gene shown in FIG. 1 encompasses a large 1.1 kilobase pair NruI and a smaller 670 base pair XmnI fragment which were both inserted into the filled out ClaI site of pPX100, to yield plasmids pPX1515 and pPX1520.

Figure 6:
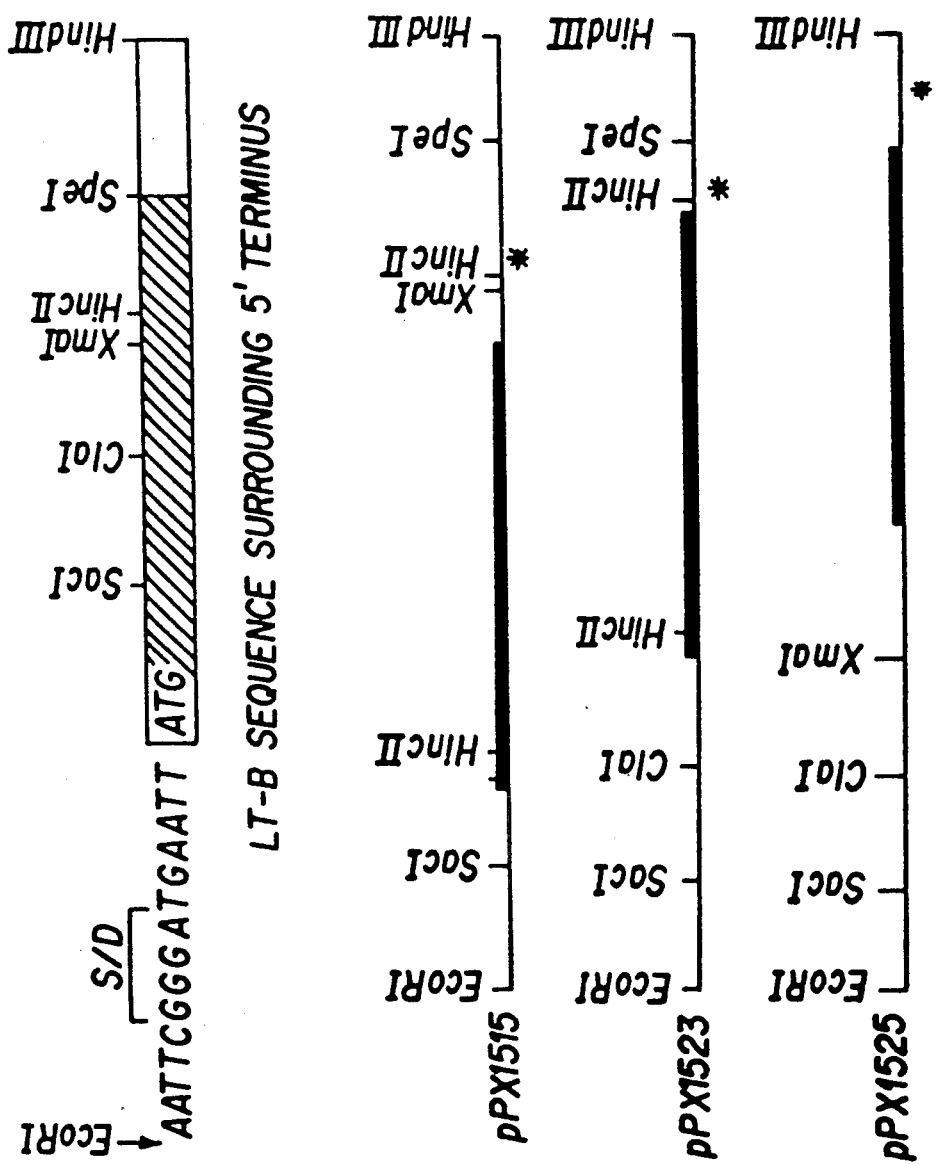

FIG. 6. Is a diagrammatic representation of portions of vectors constructed to express LT-B/CS fusion proteins regulated by the translation initiation signals of LT-B. The 670 base pair XmnI CS fragment described in FIG. 5 was inserted at the ClaI site (pPX1515), at the XmaI (pPX1523) or the SpeI (pPX1525) site of the LT-B sequence. The resulting vectors express LT-B/CS fusion proteins using the translation initiation signals of the LT-B protein. Relative positions of translation stop codons within the sequence derived from the LT-B insert are indicated by asterisks.

Figure 7:
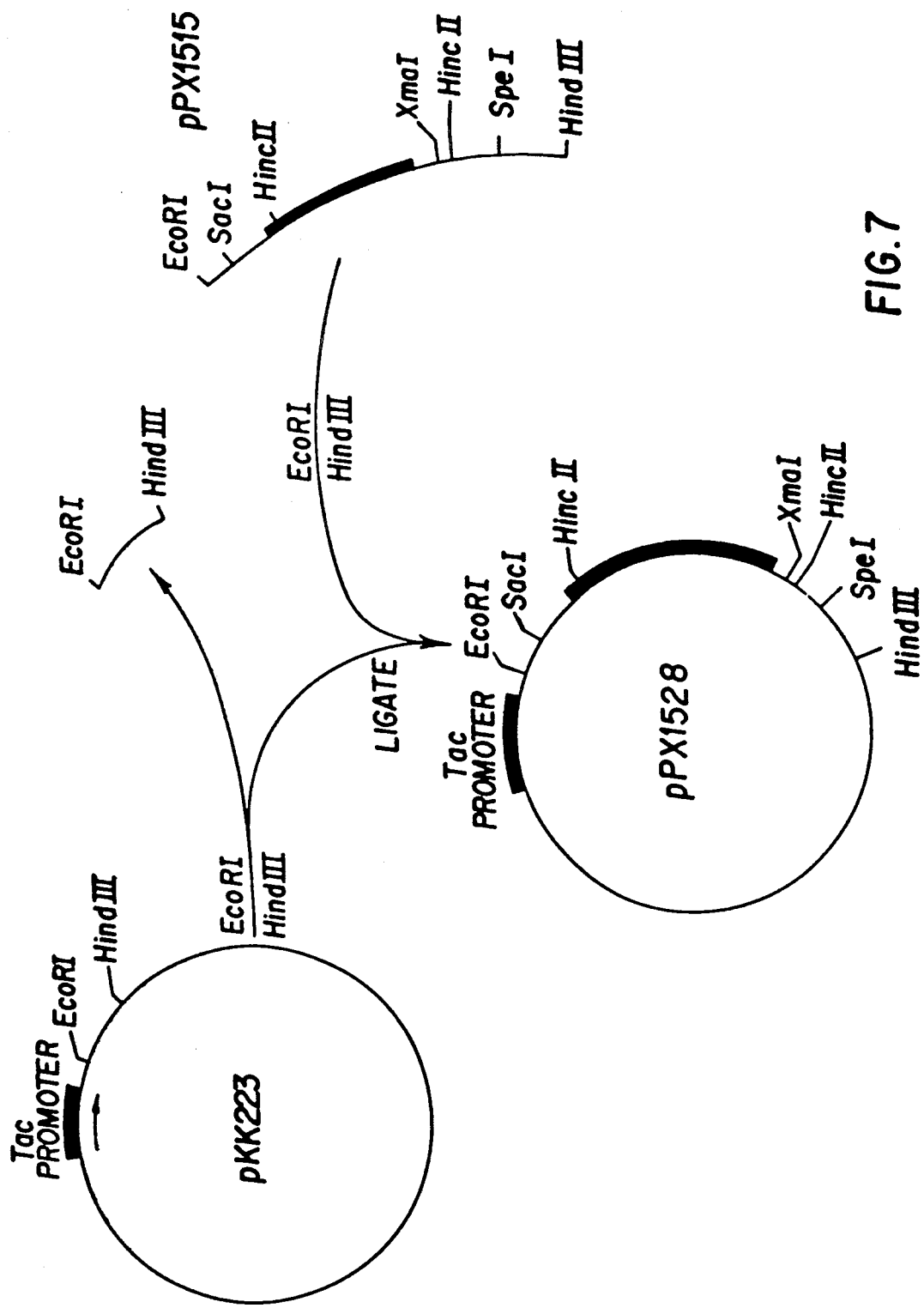

FIG. 7. Is a diagrammatic representation of the construction of tac promoter-driven LT-B/CS fusion proteins The EcoRI-HindIII restriction enzyme fragments containing the LT-B/CS fusion sequence, from either pPX1515, pPX1523, or pPX1525, were isolated and ligated into the EcoRI-HindIII sites of pKK223. The resulting plasmids can express the LT-B/CS fusion proteins under the control of the tac promoter. The construction of pPX1528 is shown as an example.

Figure 8:
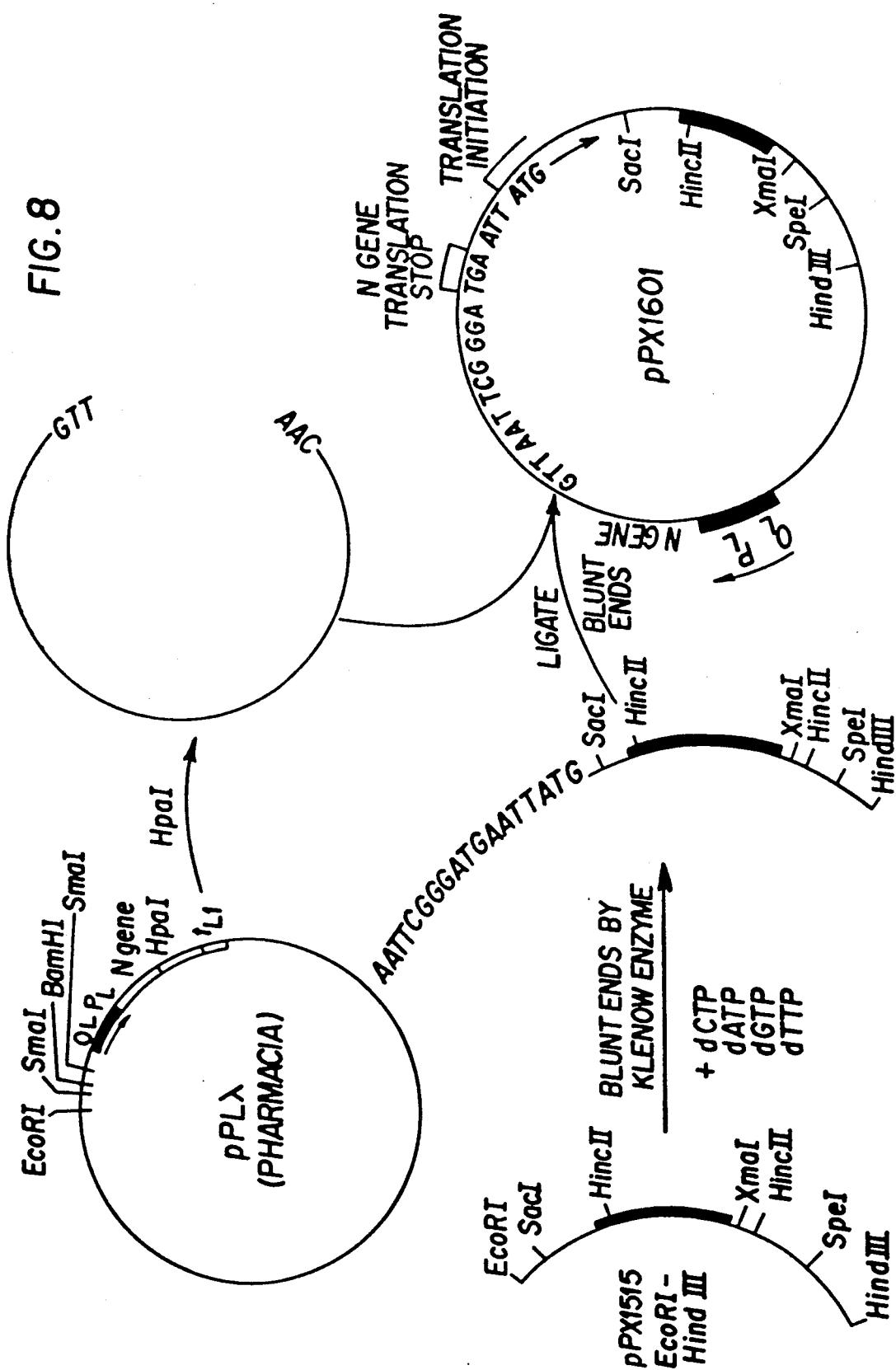

FIG. 8. Is a diagrammatic representation of the construction of PL promoter-driven LT-B/CS fusion proteins. The EcoRI-HindIII fragments, containing the LT-B/CS fusion sequences, isolated from either pPX1515, pPX1523, or pPX1525, were "filled out" with Klenow enzyme and ligated into the HpaI site of plasmid pP$_L$ lambda. The resulting plasmids can express LT-B/CS fusion proteins under the control of the P$_L$ promoter. The construction of pPX1601 is shown as an example.

Figure 9:
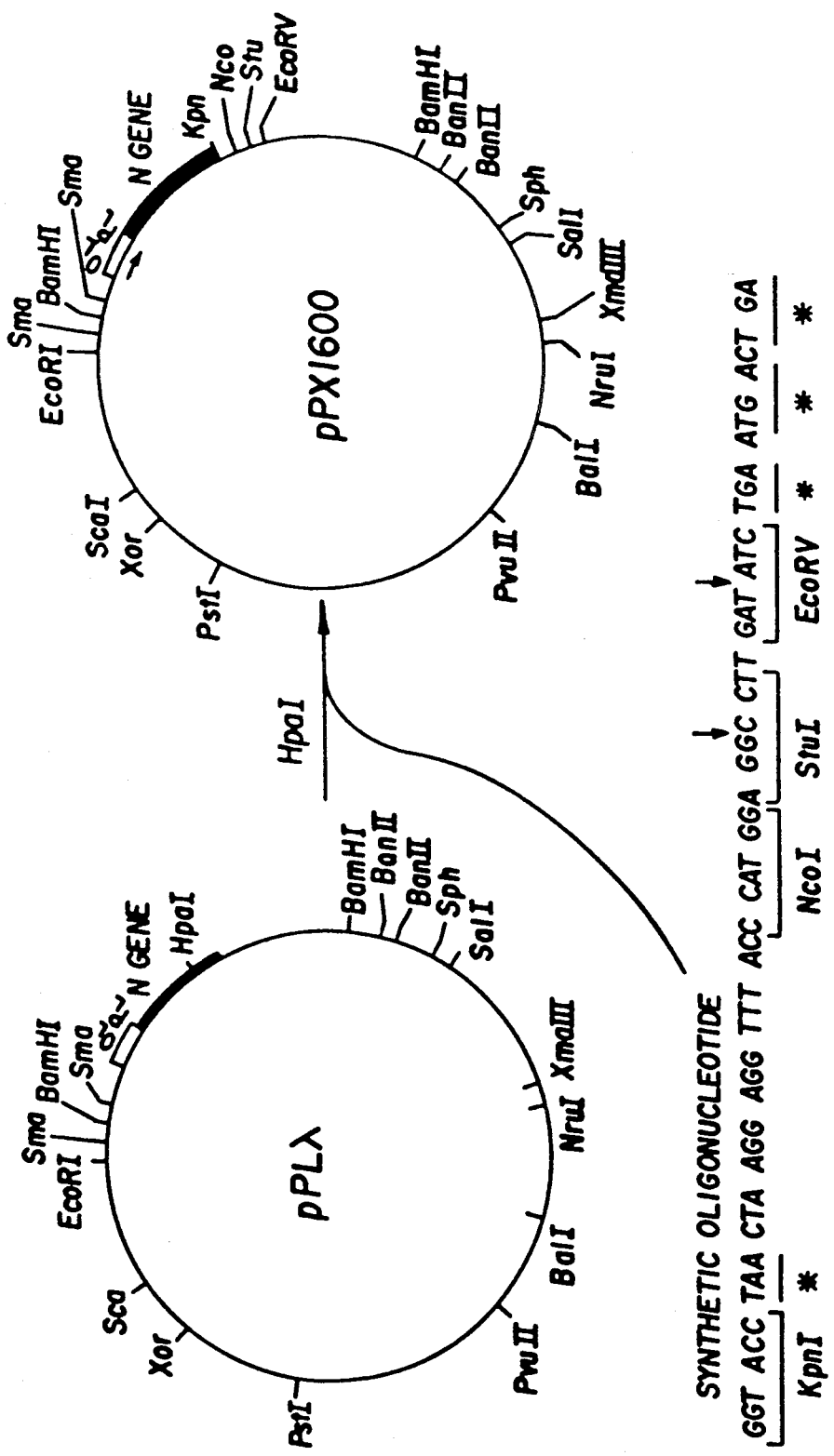

FIG. 9. Is a diagrammatic representation of the construction of P$_L$ promoter-driven expression vector pPX1600. An oligonucleotide encoding several restriction enzyme sites, a consensus Shine-Dalgarno sequence, a translation initiation codon, and translation termination codons in all three reading frames was synthesized and ligated into the HpaI site of pP$_L$ lambda to yield pPX1600. pPX1600 can be used to conveniently insert and express heterologous sequences under the control of the P$_L$ promoter.

Figure 10:
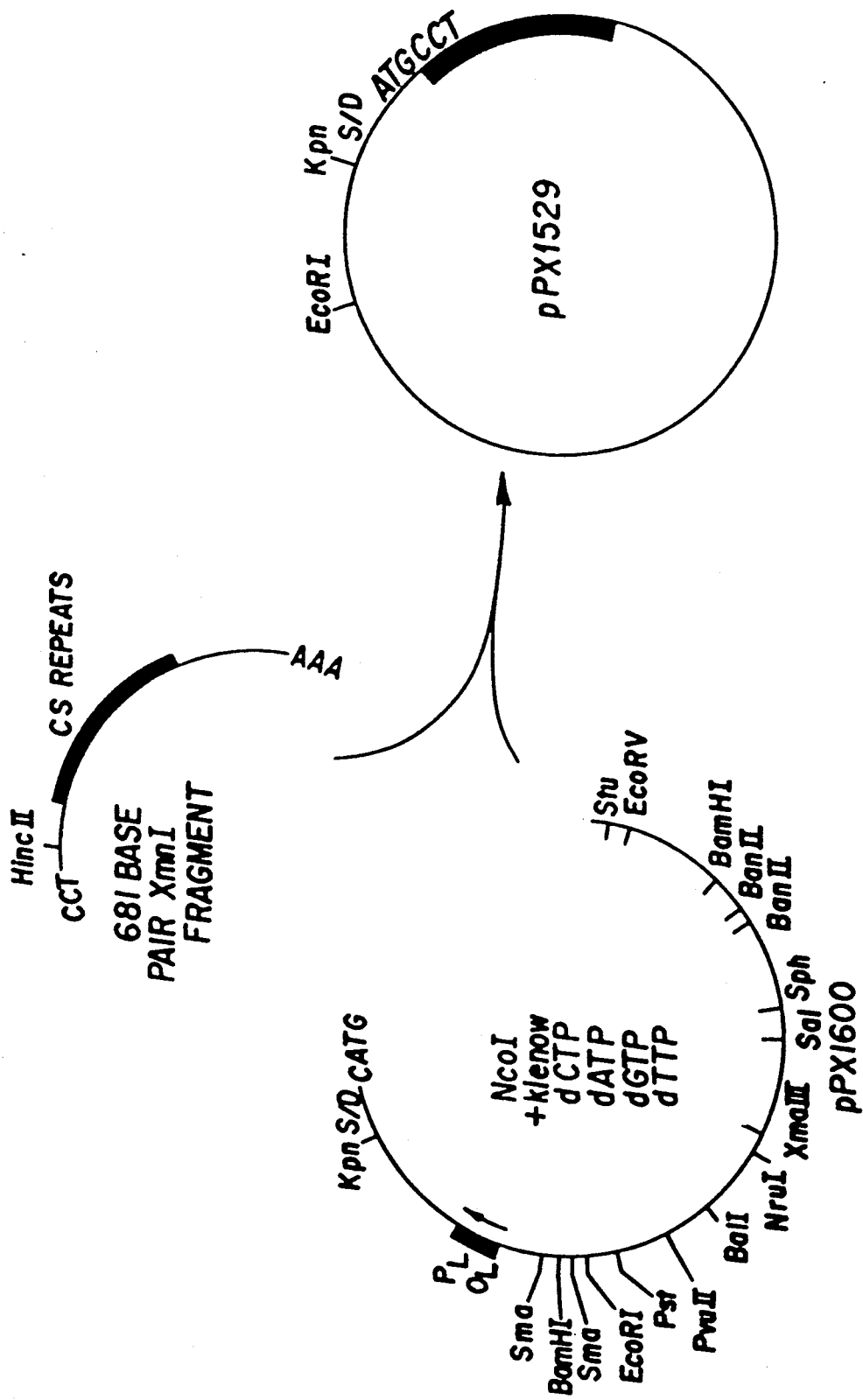

FIG. 10. Is a diagrammatic representation of the construction of a plasmid vector containing the P. berghei CS gene driven by the P$_L$ promoter. The 670 base pair XmnI fragment of the P. berghei CS gene was isolated and ligated directly into the filled out NcoI site of plasmid pPX1600 to yield pPX1529. Plasmid pPX1529 can express the P. berghei CS gene sequence under the control of the P$_L$ promoter.

Figure 11:
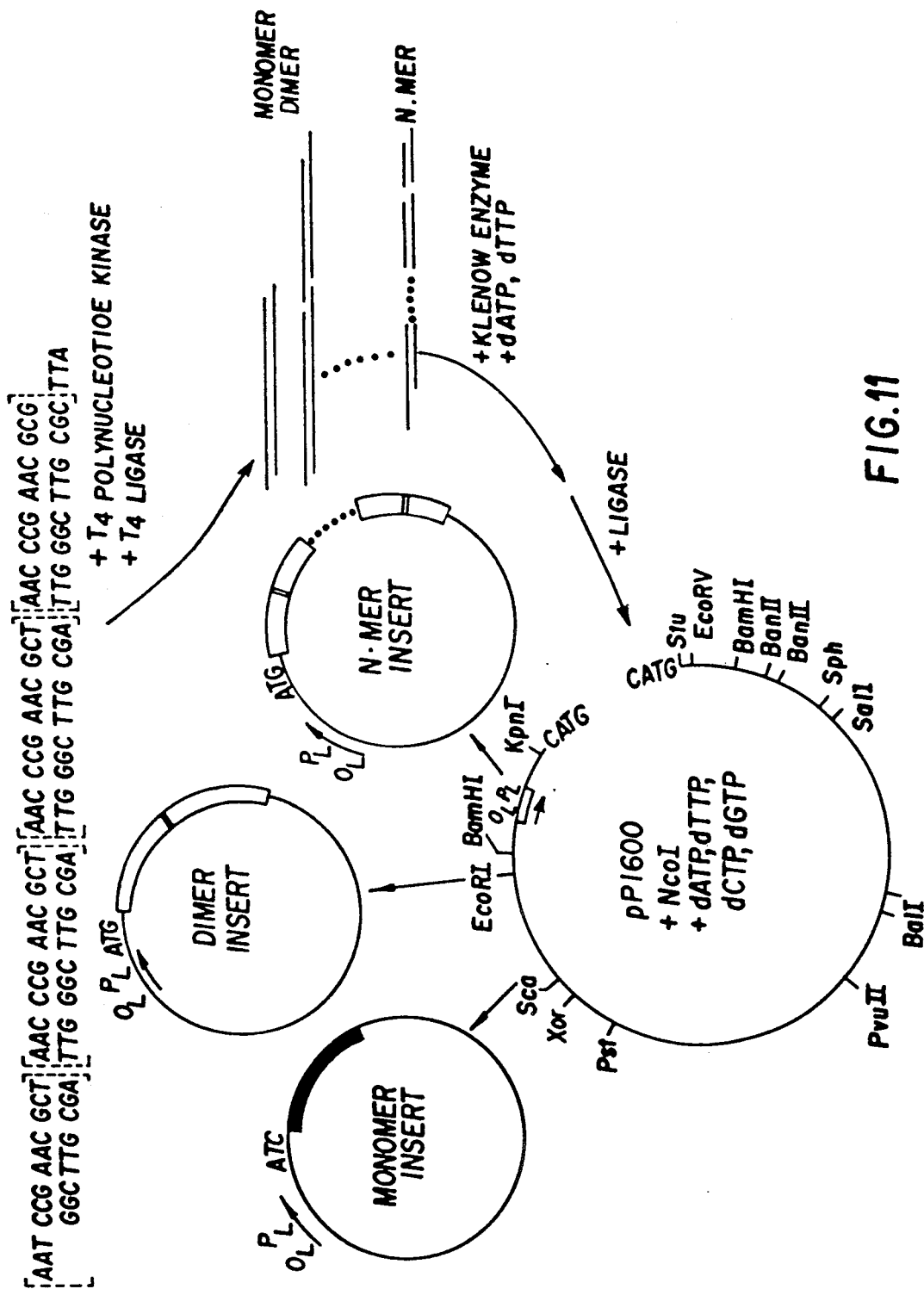

FIG. 11. Is a diagrammatic representation of the construction of plasmid vectors which encode immunodominant epitopes of P. falciparum or P. berghei CS protein, driven by the P$_L$ promoter. By ligating polymerized oligonucleotides encoding CS epitopes (obtained as described in Section 7.7, infra), into the filled out NcoI site of pPX1600, various plasmids containing the oligonucleotides as inserts were isolated. For purposes of demonstration, the insertion of an oligonucleotide encoding four repeats of the P. falciparum CS epitope is shown. A monomeric insert results from the insertion of one copy of the oligonucleotide into the NcoI site. The resulting plasmids can express CS epitopes under the control of the P$_L$ promoter.

Figure 12:
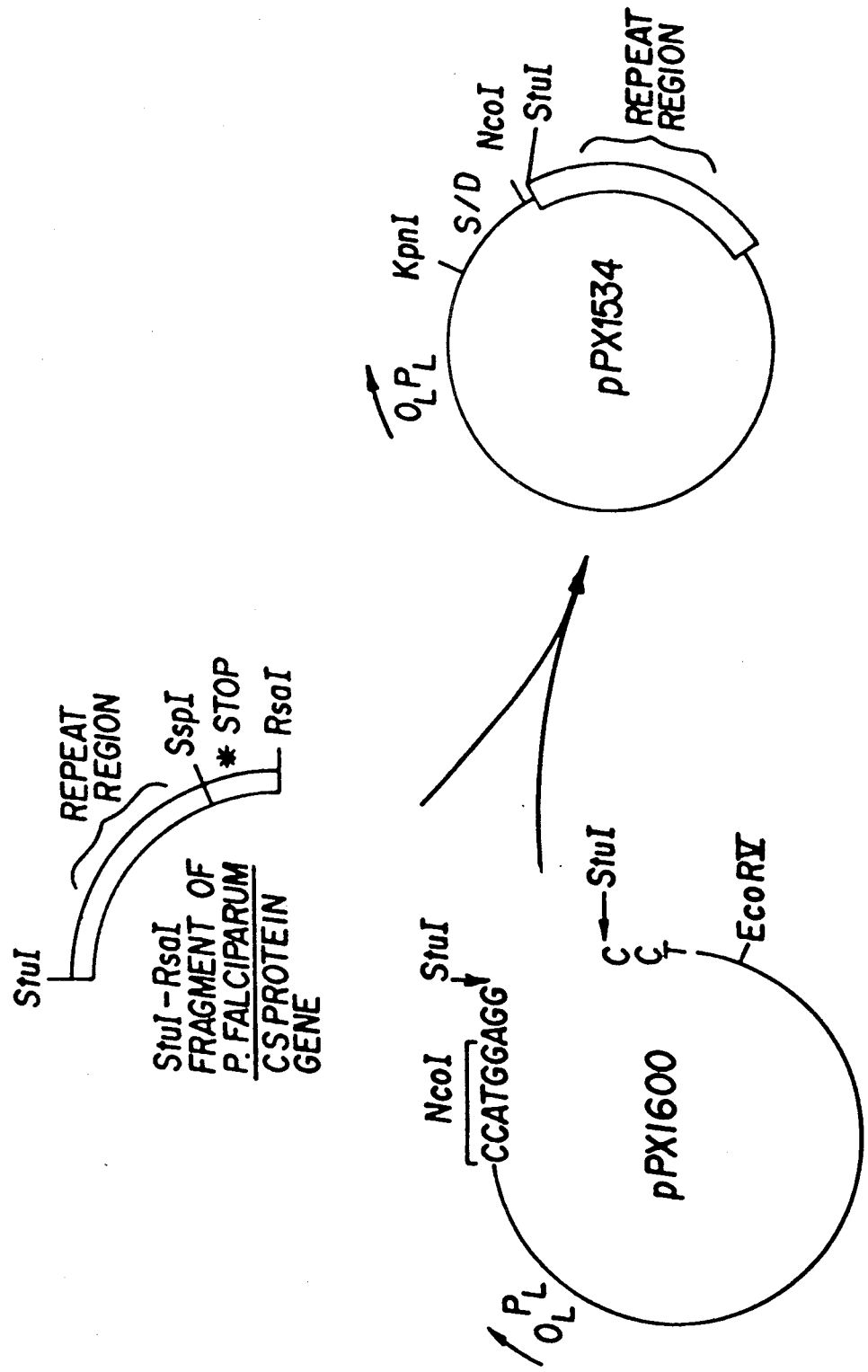

FIG. 12. Is a diagrammatic representation of the construction of a plasmid vector which can express the full length P. falciparum CS protein gene under the control of the P$_L$ promoter. The StuI-RsaI DNA fragment of the P. falciparum CS protein gene was ligated into the StuI site of plasmid pPX1600 to yield plasmid pPX1534, which expresses the full length CS gene (lacking only a region encoding the putative 16 amino acid signal sequence) from the P$_L$ promoter.

Figure 13:
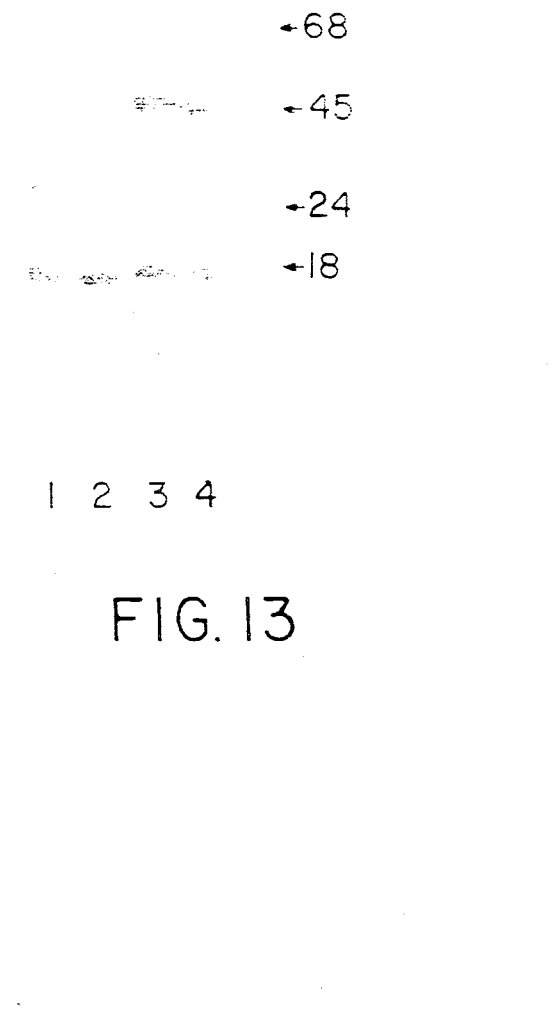

FIG. 13. Expression of LT-B/CS fusion protein in S. dublin SL1438 with increasing strength of promoter. The gene encoding a fusion protein in which 30 amino acids of mature LT-B is fused in-frame with 223 amino acids of the P. berghei CS protein, was linked, using the same translation initiation signals, to different promoters. Proteins were separated by SDS-polyacrylamide gel electrophoresis and transferred to nitrocellulose for detection of CS protein with anti-CS mAb 3.28, in a western blotting procedure. The following vectors were expressed in S. dublin SL1438: Lane 1, vector pUC8; Lane 2, pPX1515 (lac promoter); Lane 3, pPX1528 (tac promoter); Lane 4, pPX1601 (P$_L$ promoter). The arrow indicates the position of the CS protein.

Figure 14:
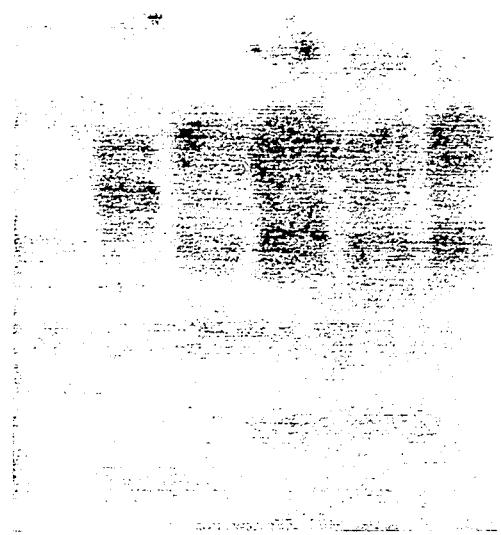

FIG. 14. Expression in Salmonella dublin of betagalactosidase/CS or LT-B/CS fusion proteins driven by the lac promoter. Proteins synthesized in S. dublin SL1438 were separated by SDS-polyacrylamide gel electrophoresis, and transferred to nitrocellulose for detection of the CS-specific epitope with anti-CS mAb 3.28, in a western blotting procedure. The following vectors were expressed in S. dublin SL1438: Lane 1, vector pUC8; Lane 2, pPX1512; Lane 3, pPX1514; Lane 4, pPX1515; Lane 5, pPX1520; Lane 6, pPX1522. (For a description of each of the plasmid constructions, see Sections 7.1-7.9, infra).

Figures 15A, 15B:

FIG. 15. Expression of LT-B/CS P. berghei fusion protein, under the control of various promoters, in S. typhimurium, S. dublin, and S. typhi. aroA mutants of the indicated Salmonella strains were grown to midlog phase in Luria broth containing 50 micrograms per ml of ampicillin. Total protein samples were subjected to electrophoresis in SDS-PAGE and western blotting as described in Sections 6.9 and 6.10. The arrows on the left indicate protein molecular weights expressed in kiloDaltons; the arrow on the right indicates the position of the LT-B/CS fusion protein.

FIG. 16. Isoelectric focussing of proteins obtained from E. coli and Salmonella strains which express the P. falciparum repeat epitope fused to the first thirty amino acids of LT-B. Sonicated extracts of the indicated strains, containing approximately 50 micrograms of protein, were subjected to isoelectric focussing in a vertical gel apparatus as described in Section 6.10. Ty523 is an S. typhi aroA mutant; SL3261 is an S. typhimurium aroA mutant, and SL1438 is an S. dublin aroA mutant. E. coli strain JM103 containing plasmid pPX1532 was induced with 1 mM IPTG; as a control, the same strain without IPTG induction is shown. The principal immunoreactive species are indicated by arrows at the right.

Figure 17:
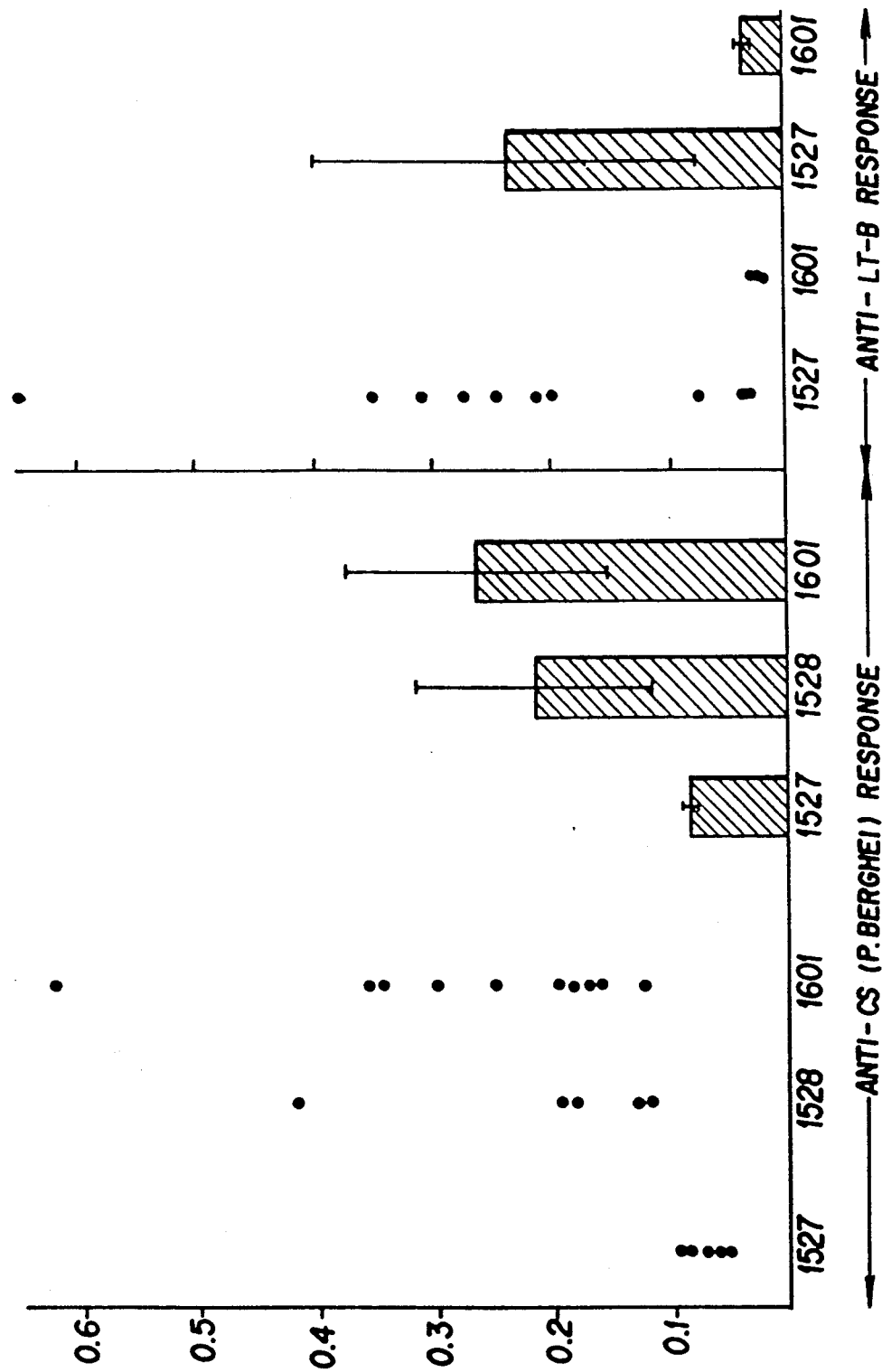

FIG. 17. Anti-CS protein serum antibody response to recombinant Salmonella dublin SL1438 expressing an LT-B/CS fusion protein, or LT-B. C57bl/6 mice received a primary vaccinating dose of $10^7$ S. dublin carrying the indicated plasmids by the intraperitoneal (i.p.) route. Mice were boosted i.p. at week 4 with organisms of the same strain as the primary dose. Anti-CS protein antibody response was measured in an ELISA with a 1:160 dilution of serum taken at week four. Data are expressed as OD (optical density) values measured at 410 nm. pPX1527 encodes LT-B driven by the tac promoter; pPX1528 encodes an LT-B/CS fusion protein driven by the tac promoter; and pPX1601 encodes an LT-B/CS fusion protein driven by the P$_L$ promoter.

5. DETAILED DESCRIPTION OF THE INVENTION

The present invention is directed to attenuated strains of enteroinvasive bacteria that express peptides and proteins related to epitopes of the malaria parasites of the genus Plasmodium. The bacterial strains of the present invention which can multiply in a host without causing significant disease or disorder, and which express Plasmodium-related peptides that induce a protective immune response against malaria, can be used in live vaccine formulations for malaria. Such vaccine formulations can be univalent or multivalent.

The expression of Plasmodium epitopes in the vaccine formulations of the present invention provides protective immunity against malaria due to the ability of such vaccine formulations to evoke a cell-mediated immune response in addition to a humoral response. Cell-mediated immunity directed against the Plasmodium epitope results from the invasive properties of the bacteria, which allow presentation of the epitope to the host immune system in a manner which can induce cell-mediated immunity.

In particular, the vaccine vector strains of the present invention comprise attenuated Salmonella bacteria which retain their enteroinvasive properties but lose in large part their virulence properties. Bacteria of the genus Salmonella can invade intestinal epithelial cells and establish systemic infections by invading the reticuloendothelial system of the host animal. By causing attenuation of virulent bacteria, invasive properties of the bacteria are retained but their virulence properties are lost.

In a preferred embodiment of the invention, a gene or gene fragment encoding all or part of the circumsporozoite malaria antigen can be expressed in Salmonella bacteria that have been attenuated by chromosomal deletion of gene(s) for aromatic compound biosynthesis, for use as a live vaccine for malaria.

By obtaining expression of the circumsporozoite proteins of the malarial sporozoites in attenuated Salmonella, sporozoite antigens can be effectively delivered to the specific cells important in immune recognition by bacterial invasion without bacterial persistence or virulence. In this fashion, effective vaccines against malaria sporozoites can be achieved.

The present invention also relates to the methods for expression of the malaria proteins or fragments thereof within attenuated enteroinvasive bacteria. The invention also demonstrates the use of plasmid vectors designed for malaria peptide or protein expression in attenuated enteroinvasive bacteria. In particular embodiments, this invention is directed to methods of obtaining expression of circumsporozoite proteins in attenuated Salmonella spp. and relates to DNA sequences encoding the circumsporozoite proteins of *P. falciparum, P. vivax, P. ovale, P. malariae, P. berghei, P. yoelii, P. knowlesi*, and *P. cynomolgi*. The circumsporozoite proteins of the above species of Plasmodium can be expressed in an attenuated Salmonella strain which is enteroinvasive in the animal host for the appropriate malaria parasite. In a specific embodiment, the invention also relates to the expression of the *P. falciparum* circumsporozoite protein or immunogenic portion thereof in attenuated *S. typhi* containing aroA chromosomal deletion mutation(s), for use as a live vaccine against the most serious form of human malaria. In another specific embodiment, the invention relates to the expression of *P. berghei* circumsporozoite protein in attenuated Salmonella which are enteroinvasive for mice, as a model system to study the efficacy of the live vaccines of the present invention for human malaria.

In another embodiment, the invention relates to the expression of malaria proteins as recombinant fusion proteins. Such fusion proteins can exhibit increased immunogenicity of malaria epitopes. In a particular embodiment, by obtaining fusion circumsporozoite proteins using recombinant DNA technology, the immunogenicity of the circumsporozoite protein can be modified. In such an embodiment, DNA encoding the circumsporozoite protein or an epitope thereof can be joined to the gene for the B-subunit of the labile enterotoxin of *E. coli* (LT-B), or a portion thereof, in order to achieve modified immunogenicity. Fusion LT-B/circumsporozoite protein immunogens expressed in Salmonella spp. can supply additional T cell helper functions. In this embodiment, coupling of an epitope of the circumsporozoite protein to LT-B also directs the recombinant DNA-derived fusion protein to the periplasmic space of the invasive Salmonella, and aids in antigen presentation.

The method of the invention may be divided into the following stages solely for the purpose of description: (a) isolation of a gene, or gene fragment, encoding an epitope of a malaria parasite; (b) insertion of the gene or gene fragment into an expression vector; (c) transfer to and expression of the gene or gene fragment in an attenuated enteroinvasive bacteria; (d) determination of immunopotency of the malaria epitope expressed by the recombinant enteroinvasive bacteria; and (e) formulation of a vaccine.

In specific embodiments of the present invention described in the examples sections herein, we describe the construction of recombinant plasmid expression vectors encoding epitopes of the circumsporozoite protein of *P. berghei*, or of *P. falciparum*. We further describe the expression of recombinant LT-B/CS fusion proteins in attenuated Salmonella strains. The recombinant Salmonella which express CS peptides are shown to elicit anti-CS antibody production in mice, and to provoke immune responses which protect against malaria infection upon sporozoite challenge.

5.1. ISOLATION OF GENE OR GENE FRAGMENTS ENCODING PLASMODIUM EPITOPES

Any DNA sequence which encodes a Plasmodium epitope, which when expressed as a fusion or nonfusion protein in an attenuated enteroinvasive bacteria, produces protective immunity against malaria, can be isolated for use in the vaccine formulations of the present invention. The species of Plasmodium which can serve as DNA sources include but are not limited to the human malaria parasites *P. falciparum, P. vivax, P. ovale, P. malariae*, and the animal malaria parasites *P. berghei, P. yoelii, P. knowlesi*, and *P. cynomolgi*.

There are numerous genes which encode a Plasmodium antigen that can serve as a source of the DNA sequence to be isolated and expressed in attenuated enteroinvasive bacteria according to the present invention. The antigens, or fragments thereof, which can be expressed by recombinant bacteria in the vaccine formulations of the invention are antigens which are expressed by the malaria parasite at any of the various stages in its life cycle, such as the sporozoite, exoerythrocytic (development in hepatic parenchymal cells), asexual erythrocytic, or sexual (e.g., gametes, zygotes, ookinetes) stages. The antigen can be expressed by the malaria parasite itself or by an infected cell. The Plasmodium antigens which may be used include but are not limited to those described in the following publications, incorporated by reference herein:

Vaccines85, 1985, Lerner, R. A., et al., eds., Cold Spring Harbor Laboratory, Cold Spring Harbor, N.Y., pp. 1-57
Vaccines86, 1986, Brown, F., et al., eds., Cold Spring Harbor Laboratory, Cold Spring Harbor, N.Y., pp. 135-179
Vaccines87, 1987, Channock et al., eds., Cold Spring Harbor Laboratory, Cold Spring Harbor, New York, pp. 81-106, 117-124
Kemp, D. J., et al., 1983, Proc. Natl. Acad. Sci. U.S.A. 80:3787
Anders, R. F., et al., 1984, Mol. Biol. Med. 2(3):177-191
Miller, L. H., et al., 1984, J. Immunol. 132(1):438-442
Carter, R., et al., Nov. 13, 1984, Philos. Trans. R. Soc. Lond. (Biol.) 307(1131):201-213
Holder, A. A. and Freeman, R. R., 1981, Nature 294:361
Leech, J. H., et al., 1984, J. Exp. Med. 159:1567
Rener, J., et al., 1983, J. Exp. Med. 158:971
Dame, J. B., et al., 1984, Science 225:593
Arnot, D. E., et al., 1985, Science 230:815
Coppel, R. L., et al., 1983, Nature 306:751
Coppel, R. L., et al., 1984, Nature 310:789
Holder, A. A., et al., 1985, Nature 317:270
Ardeshir, F., et al., 1987, EMBO J. 6:493
Ravetch, J. V., et al., 1985, Science 227:1593
Stahl, H.-D., et al., 1985, Proc. Natl. Acad. Sci. U.S.A. 82:543
Langsley, G., et al., 1985, Nucl. Acids Res. 11:4191
Coppel, R. L., et al., 1985, Proc. Natl. Acad. Sci. U.S.A. 82:5121
Howard, R. J., et al., 1987, J. Cell Biol. 104:1269
Buranakitjaroen, P. and Newbold, C. I., 1987, Mol. Biochem. Parasitol. 22:65
Schofield, L., et al., 1986, Mol. Biochem. Parasitol. 18:183
Knowles, G. and Davidson, W. L., 1984, Am. J. Trop. Med. Hyg. 33:789
Kilejian, A., 1979, Proc. Natl. Acad. Sci. U.S.A. 76:4650
Leech, J. H., et al., 1984, J. Cell. Biol. 98:1256
Hadley, T. J., et al., 1986, Ann. Rev. Microbiol. 40:451
Camus, D. and Hadley, T. J., 1985, Science 230:553
Vermeulen, A. M., et al., 1985, J. Exp. Med. 162:1460.
Vermeulen, A. M., et al., 1986, Mol. Biochem. Parasitol. 20:155
Kumar, N. and Carter, R., 1984, Mol. Biochem. Parasitol. 13:333
Patarroyo, M. E., et al., 1987, Nature 328:629-632
Miller, L. H., et al., 1984, Phil. Trans. R. Soc. Lond. B307:99-115.

As particular examples, such antigens include the circumsporozoite antigen; the *P. falciparum* blood-stage ring-infected erythrocyte surface antigen (RESA), S antigen, Falciparum interspersed repeat antigen (FIRA), glycophorin binding protein (GBP), Pf 195 kD antigen, circumsporozoite protein-related antigen (CRA), Pf 155 antigen, Pf 75 kD antigen, Pf EMP 2 antigen, and Pf knob-associated antigens; *P. falciparum* sexual stage antigens of 260,000, 59,000 and 53,000 molecular weight, antigens of 230,000, 48,000, and 45,000 molecular weight, etc.

In a particular embodiment, a Plasmodium peptide can be expressed as a fusion protein with a secreted protein sequence of a bacteria, so that the recombinant fusion protein is directed to the periplasmic space of the bacteria, thus aiding presentation to the immune system and enhancing immunogenicity.

Although extracellular localization of the Plasmodium epitope expressed by the recombinant enteroinvasive bacteria is preferred, extracellular localization is not required, since intracellular localization can also evoke an effective immune response. When beta-galactosidase, an intracellular protein, was expressed in *S. typhimurium* SL3261, specific anti-beta-galactosidase antibodies were elicited by administration of the recombinant bacteria to mice (Brown, A., et al., 1987, J. Inf. Disc. 155:86).

In a preferred embodiment, the malaria epitope to be expressed is an epitope of the circumsporozoite (CS) protein of a species of Plasmodium. Analogous CS proteins have been identified on the surfaces of sporozoites of all serotypes of Plasmodium. Circumsporozoite protein antigens expressed in attenuated Salmonella spp. can be used as live vaccines directed against sporozoites, the invasive form of malaria parasites transmitted by the female Anopheles mosquito. The genes which encode a CS epitope and which those Plasmodium species listed supra. In particular, those genes encoding the CS proteins of the human malaria parasites *P. falciparum*, *P. vivax*, the simian parasites *P. cynomolgi* and *P. knowlesi*, and the rodent parasite *P. berghei* can be used; these genes have been cloned and sequenced, as reported in the following publications, which are incorporated by reference herein: Dame, J. B., et al., 1984, Science 225:593; Arnot, D. D., et al., 1985, Science 230:815; Weber et al., 1987, Exp. Parasitol. 63:295; Enea, V., et al., 1984, Science 225:628; Enea, V., et al., 1984, Proc. Natl. Acad. Sci. U.S.A. 81:7520; Godson, G. N., et al., 1983, Nature 305:29; and McCutchan, T. F., et al., 1985, Science 230:1381. A characteristic feature of the CS genes of each of the parasites is a central region which comprises over one third of the protein and contains a large series of repeated peptide sequences (Dame, J. B., et al., 1984, Science 225:593; Ozaki, L. S., et al., 1983, Cell 34:815). The primary amino acid sequence, the length of the repeating sequence, and the number of repeats varies with each species of parasite. As examples, the gene encoding the CS protein of *P. falciparum* specifies a central repeat region of a tetrapeptide (asn-ala-asn-pro) repeated thirty-seven times, interrupted in four locations by a variant tetrapeptide (asn-val-asp-pro). The central repeat region of *P. vivax* contains nineteen nonapeptides; the central sequence of *P. knowlesi* contains eight dodecapeptides, and the repeat region of *P. berghei* contains twelve octapeptides. Comparison of sequences from *P. knowlesi* (H strain) and *P. falciparum* and *P. vivax* revealed no sequence homology, except for two short amino acid sequences flanking the repeat region, termed Region I and Region II. The repeat regions appear to be highly conserved within the human malaria parasites *P. falciparum* and *P. vivax* (Weber, J. L. and Hockmeyer, W. T., 1984, Mol. Biochem. Parasitol. 15:305; Zavala, F., et al., 1985, J. Immunol. 135:2750), though intra-species variation has been observed in *P. knowlesi* and *P. cynomolgi*. The repeat region also appears to be immunodominant (Dame, J. B., et al., 1984, Science 225:593; Hockmeyer, W. T. and Dame, J. B., 1985, in Immunobiology of Proteins and Peptides III, Atassi, M. Z., ed., Plenum Press, New York, pp. 233-246; Zavala, F., et al., 1983, J. Exp. Med. 157:1947; Zavala, F., et al., 1985, Science 228:1436). In preferred embodiments of the invention, DNA sequences containing the repeat region, Region I, or Region II, can be isolated for use in the vaccine formulations of the present invention. For example, in one embodiment, the peptide asn-ala-asn-pro, related to the *P. falciparum* CS repeat region, can be expressed by the recombinant bacteria of the invention. In another embodiment, the peptide asp-pro-ala-pro-pro-asn-ala-asn, representing the *P. berghei* CS protein repeat region, can be expressed.

The Plasmodium CS peptides to be expressed in recombinant enteroinvasive bacteria according to the present invention, whether produced by recombinant DNA methods, chemical synthesis, or purification techniques, include but are not limited to all or part of the amino acid sequences of Plasmodium-specific antigens, including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic and glutamic acid.

A DNA sequence encoding a malarial epitope which is a hapten, i.e., a molecule that is antigenic in that it can react selectively with cognate antibodies, but not immunogenic in that it cannot elicit an immune response, can be isolated for use in the vaccine formulations of the present invention, since it is envisioned that, in particular embodiments, presentation by the enteroinvasive attenuated bacteria of the invention can confer immunogenicity to the hapten expressed by the bacteria. As particular examples, expression of a malarial hapten as a fusion protein with an immunogenic peptide, e.g., derived from *E. coli* enterotoxin subunit B (LT-B), can confer immunogenicity.

5.2. CONSTRUCTION OF EXPRESSION VECTORS CONTAINING SEQUENCES WHICH ENCODE A PLASMODIUM EPITOPE

In this aspect of the invention, the desired DNA sequence encoding the malarial epitope is inserted, using recombinant DNA methodology (see Maniatis, T., 1982, Molecular Cloning, A Laboratory Manual, Cold Spring Harbor Laboratory, Cold Spring Harbor, N.Y.), into an expression vector so that it can be expressed under the control of an active promoter in the host attenuated enteroinvasive bacteria. The DNA sequence encoding the Plasmodium epitope can be obtained from any of numerous sources such as cloned malarial DNA, genomic malarial DNA, cDNA of malarial RNA, or chemically synthesized DNA.

In order to generate Plasmodium DNA fragments, the Plasmodium DNA may be cleaved at specific sites using various restriction enzymes. Alternatively, one may use DNaseI in the presence of manganese, or mung bean nuclease (McCutchan et al., 1984, Science 225:626), to fragment the DNA, or the DNA can be physically sheared, as for example, by sonication. The linear DNA fragments can then be separated according to size by standard techniques, including, but not limited to, agarose and polyacrylamide gel electrophoresis and column chromatography.

Any restriction enzyme or combination of restriction enzymes may be used to generate Plasmodium DNA fragment(s) containing the desired epitope(s), provided the enzymes do not destroy the immunopotency of the encoded product. Consequently, many restriction enzyme combinations may be used to generate DNA fragments which, when inserted into a appropriate vector, are capable of directing the production of the peptide containing the Plasmodium epitope.

Once the DNA fragments are generated, identification of the specific DNA fragment containing the desired malaria sequence may be accomplished in a number of ways. For example, if a small amount of the desired DNA sequence or a homologous sequence is previously available, it can be used as a labeled probe (e.g., nick translated) to detect the DNA fragment containing the desired sequence, by nucleic acid hybridization. Alternatively, if the sequence of the derived gene or gene fragment is known, isolated fragments or portions thereof can be sequenced by methods known in the art, and identified by a comparison of the derived sequence to that of the known DNA or protein sequence. Alternatively, the desired fragment can be identified by techniques including but not limited to mRNA selection, making cDNA to the identified mRNA, chemically synthesizing the gene sequence (provided the sequence is known), or selection on the basis of expression of the encoded protein (e.g., by antibody binding) after "shotgun cloning" of various DNA fragments into an expression system.

Once identified and isolated, the Plasmodium DNA fragment containing the sequence(s) of interest is then inserted into a vector which is capable of replication and expression in the host enteroinvasive bacteria. The Plasmodium DNA may be inserted into the bacterial chromosomal DNA. Alternatively, in a preferred embodiment, the Plasmodium DNA is inserted into a cloning vector which can exist episomally, e.g., a plasmid or bacteriophage, which is then used to transform or infect appropriate host bacterial cells, where the Plasmodium DNA is replicated and expressed.

If the complementary restriction sites used to fragment the Plasmodium DNA are not present in the cloning vector, the ends of the DNA molecules may be modified (for example, see Section 6, infra). Such modifications include producing blunt ends by digesting back single-stranded DNA termini or by filling the single-stranded termini so that the ends can be blunt-end ligated. Alternatively, any site desired may be produced by ligating nucleotide sequences (linkers) onto the DNA termini; these ligated linkers may comprise specific chemically synthesized oligonucleotides encoding restriction site recognition sequences. According to other methods, the cleaved vector and the Plasmodium DNA fragment may be modified by homopolymeric tailing.

The transformation of attenuated enteroinvasive bacteria with the recombinant DNA molecules that incorporate the Plasmodium DNA enables generation of multiple copies of the Plasmodium sequence. A variety of vector systems may be utilized for expression within the bacterial host, including but not limited to plasmids such as pUC plasmids and derivatives, PBR322 plasmid and derivatives, bacteriophage such as lambda and its derivatives, and cosmids. In a specific embodiment, plasmid cloning vectors which can be used include derivatives of ColEI type replicons (for additional information, see Oka et al., 1979, Mol. Gen. Genet. 172:151-159). The ColEI plasmids are stably maintained in *E. coli* and *Salmonella typhimurium* strains as monomeric molecules with a copy number of about 15-20 copies per cell. Various regulatory expression elements can be used, which are any of a number of suitable transcription and translation elements that are active in the attenuated enteroinvasive bacteria of the invention. For instance, promoters which may be used to direct the expression of the Plasmodium DNA sequence include but are not limited to the lactose operon promoter of *E. coli*, the hybrid trp-lac UV-5 promoter (tac) (DeBoer, H., et al., 1982, in Promoter Structure and Function, Rodriguez, R. L. and Chamberlain, M. J., eds., Praeger Publishing, New York), the leftward ($P_L$) and the rightward ($P_R$) promoters of bacteriophage lambda, the bacteriophage T7 promoter, the trp operon promoter, the lpp promoter (the *E. coli* lipoprotein gene promoter; Nakamura, K. and Inouye, I., 1979, Cell 18:1109-1117), etc. Other promoters produced by recombinant DNA or synthetic techniques may also be used to provide for transcription of the inserted sequences.

Specific initiation signals are also required for efficient translation of inserted protein coding sequences. These signals include the ATG initiation codon and adjacent sequences. In cases where the entire Plasmodium gene including its own initiation codon and adjacent sequences are inserted into the appropriate expression vectors, no additional translational control signals may be needed. However, in cases where only a portion of the gene sequence is inserted, exogenous translational control signals, including the ATG initiation codon, must be provided. The initiation codon must furthermore be in phase with the reading frame of the protein coding sequences to ensure translation of the entire insert. These exogenous translational control signals and initiation codons can be of a variety of origins, both natural and synthetic.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinations (genetic recombination).

For reviews on maximizing gene expression, see Roberts and Lauer, 1979, Meth. Enzymol. 68:473; and Reznikoff, W. and Gold, M., 1986, Maximizing Gene Expression, Plenum Press, New York.

The Plasmodium peptide or protein can be expressed as a fusion or nonfusion recombinant protein. *E. coli* and other bacteria contain an active proteolytic system which appears to selectively destroy "abnormal" or foreign proteins (Bukhari, A. and Zipser, D., 1973, Nature 243:238). In order to protect eucaryotic proteins expressed in bacteria from proteolytic degradation, one strategy which can be used is to construct hybrid genes in which the foreign sequence is ligated in phase (i.e., in the correct reading frame) with a procaryotic gene. Expression of this hybrid gene results in a fusion protein product (i.e., a protein that is a hybrid of procaryotic and foreign amino acid sequences). In a specific embodiment where the Plasmodium epitope is expressed as part of a fusion protein, the Plasmodium sequence can be fused to a heterologous immunogenic sequence. In a particular embodiment, the Plasmodium sequence can be fused to all or part of the *E. coli* enterotoxin subunit B.

U.S. Pat. No. 4,237,224 to Cohen and Boyer describes production of recombinant plasmids using processes of cleavage with restriction enzymes and joining with DNA ligase by known methods of ligation. These recombinant plasmids are then introduced by means of transformation and replicated in unicellular cultures including procaryotic organisms and eucaryotic cells grown in tissue culture. Because of the general applicability of the techniques described therein, U.S. Pat. No. 4,237,224 is hereby incorporated by reference into the present specification.

Another method for introducing recombinant DNA molecules into unicellular organisms is described by Collins and Hohn in U.S. Pat. No. 4,304,863, which is also incorporated herein by reference. This method utilizes a packaging/transduction system with bacteriophage vectors (cosmids).

5.3. IDENTIFICATION OF RECOMBINANT EXPRESSION VECTORS WHICH REPLICATE AND EXPRESS A PLASMODIUM ANTIGEN OR FRAGMENT THEREOF

Expression vectors containing foreign gene inserts can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to the foreign inserted gene. In the second approach, the recombinant vector/host system can be identified and selected based upon the presence or absence of certain "marker" gene functions (e.g., beta-galactosidase activity, thymidine kinase activity, resistance to antibiotics, etc.) caused by the insertion of foreign genes in the vector. For example, if the Plasmodium DNA sequence is inserted within the marker gene sequence of the vector, recombinants containing the Plasmodium insert can be identified by the absence of the marker gene function. In the third approach, recombinant expression vectors can be identified by assaying the foreign gene product expressed by the recombinant. Such assays can be based on the physical, immunological, or functional properties of the gene product. For example, an ELISA can be used to detect the presence of antigenic determinants which bind the appropriate anti-Plasmodium antibody (e.g., see Section 6.12, infra). Once the desired recombinant molecule is identified and isolated, it can be propagated and prepared in quantity by methods known in the art.

5.4. EXPRESSION BY ATTENUATED ENTEROINVASIVE BACTERIA

The expression vector comprising the malaria DNA sequence should then be transferred into an attenuated enteroinvasive bacterial cell where it can replicate and be expressed. This can be accomplished by any of numerous methods known in the art including but not limited to transformation (e.g., of isolated plasmid DNA into the attenuated bacterial host), phage transduction, conjugation between bacterial host species, microinjection, etc. In a preferred embodiment involving the use of a plasmid expression vector, the plasmid construction can be isolated and characterized first in *E. coli* K12, before transfer to a Salmonella strain, e.g., by phage transduction (Schmeiger, 1972, Mol. Gen. Genetics 119:75), because of the high transformation frequencies of *E. coli* K12 relative to those of Salmonella such as *S. typhimurium*.

Any of various attenuated enteroinvasive bacteria can be used as a vehicle to express a malaria epitope so that it is effectively presented to the host immune system, in the vaccine formulations of the present invention. The vaccine bacteria retain their invasive properties, but lose in large part their virulence properties, thus allowing them to multiply in the host without causing significant disease or disorder. Examples of enteroinvasive bacteria which, in attenuated forms, may be used in the vaccine formulations of the invention include but are not limited to Salmonella spp., enteroinvasive *E. coli* (EIEC), and Shigella spp. In a preferred embodiment, enteroinvasive bacteria which reside in lymphoid tissues such as the spleen (e.g., Salmonella spp.) are used. Such bacteria can invade gut epithelial tissue, disseminate throughout the reticuloendothelial system, and gain access to mesenteric lymphoid tissue where they multiply and induce humoral and cell-mediated immunity.

Attenuated enteroinvasive bacteria may be obtained by numerous methods including but not limited to chemical mutagenesis, genetic insertion, deletion (Miller, J., 1972, Experiments in Molecular Genetics, Cold Spring Harbor Laboratory, Cold Spring Harbor, N.Y.) or recombination using recombinant DNA methodology (Maniatis, T., 1982, Molecular Cloning, A Laboratory Manual, Cold Spring Harbor Laboratory, Cold Spring Harbor, N.Y.), laboratory selection of natural mutations, etc. Methods for obtaining attenuated Salmonella strains which are non-reverting non-virulent auxotrophic mutants suitable for use as live vaccines are described in copending U.S. patent application Ser. Nos. 675,381, filed Nov. 27, 1984, and 798,052, filed Nov. 14, 1985, by Stocker, which are incorporated by reference herein in their entirety.

Attenuated Salmonella which can be used in the live vaccine formulations of the invention include but are not limited to those species listed in Table I, infra.

TABLE I

SALMONELLA SPECIES WHICH, IN ATTENUATED FORMS, CAN BE USED IN THE VACCINE FORMULATIONS OF THE PRESENT INVENTION*

*S. typhi*
(e.g., Ty21a, Ty523, Ty541)
*S. typhimurium*
(e.g., SL3261, LT241)
*S. paratyphi* A
*S. paratyphi* B
*S. enteritidis*
(e.g., serotype dublin, e.g., strain SL1438)
*S. cholerae-suis*

*For a complete description of Salmonella serotypes, see Edwards and Ewing, 1986, Classification of the Enterobacteriaceae, 4th Ed., Elsevier, N.Y.

In specific embodiments, Salmonella bacteria that have been attenuated by chromosomal deletion of gene(s) for aromatic compound biosynthesis (aro) or mutation in the galE gene can be used.

*S. typhi* strains such as Ty523 and Ty541 are avirulent in humans by virtue of attenuation by deletion of the genes encoding aroA and/or purA (Levine, M. M., et al., 1987, J. Clin. Invest. 79:888). Mutants of *S. dublin*, such as SL1438, and of *S. typhimurium*, such as SL3261, can be used in the development of animal model systems, since they are capable of causing animal diseases equivalent to typhoid

5.4.1. ATTENUATION BY galE MUTATIONS galE mutants can provide a source of attenuated bacteria for use in the vaccine formulations of the present invention. Such galE mutants include but are not limited to the *Salmonella typhi* strains Ty2, Ty21 (Hone et al., 1987, J. Inf. Dis. 156:167), and CDC10-80, and the *Salmonella typhimurium* strains LT-2, LT241, etc. The *S. typhi* galE mutant, Ty21a, and the *S. typhimurium* galE mutant, LT241, are lacking the enzyme UDP-galactose-epimerase and are deficient in two other enzymes of galactose metabolism (Germanier, R. and Furer, E., 1975, J. Infect. Dis. 131:553). LPS (lipopolysaccharide) is synthesized in this strain, but toxic galactose-1-phosphate accumulates and cell lysis ensues.

5.4.2. ATTENUATION BY aro MUTATIONS aro mutants provide another potential source of attenuated bacteria. Deletions of the gene aroA result in pleiotropic requirements for phenylalanine, tryptophan, tyrosine, and the folic acid precursor, p-aminobenzoic acid, and the enterochelin precursor, dihydroxybenzoic acid. The aromatic amino acids are present in animal tissues, but p-aminobenzoic acid is absent; folic acid which may be present in animal cells is not assimilated by members of the Enterobacteriaceae. In addition, absence of enterochelin results in a requirement for iron in aroA Salmonella vaccine strains (Stocker, B. A. D., et al., 1982, Develop. Biol. Standard 53:47). Thus, deletions in the aroA gene result in biochemical lesions which presumably do not affect other factors which may be important for invasiveness, thus yielding attenuated bacteria which retain invasive properties.

aro mutants which can be used include but are not limited to *S. typhi* strains Ty523 and Ty541, for use in vaccines for humans, and *S. typhimurium* SL3261 and SL1479, and *S. enteritidis* serotype *dublin* SL1438, for use in animals. (See U.S. Pat. No. 4,550,081 for a description of *S. typhimurium* strain SL1479 and *S. dublin* strain SL1438.)

A reliable method to achieve attenuation of Salmonella has been described (Hoiseth, S. K. and Stocker, B. A. D., 1981, Nature 291:238; Stocker, B. A. D., et al., 1982, Develop. Biol. Standard 53:47; and U.S. Pat. No. 4,550,081) and can be used in a particular embodiment of the invention. In this method, specific deletion mutations affecting the aromatic biosynthetic pathway are introduced by transduction. The advantage of this method is that precisely defined mutations can be engineered without the use of chemical or radiation mutagenesis. In principle, a defect in aromatic biosynthesis in Salmonella causes requirements for nutrients not present in adequate free concentrations in animal tissues to support the growth of the bacteria; hence, invading bacteria are attenuated and cannot cause disease. Because mutations are deletions of a large part of one or more genes, mutational reversion is improbable.

5.5. DETERMINATION OF IMMUNOPOTENCY OF THE PLASMODIUM EPITOPE EXPRESSED BY THE RECOMBINANT ENTEROINVASIVE BACTERIA

Immunopotency of the malaria epitope in its live vaccine formulation can be determined by monitoring the immune response of test animals following immunization with the attenuated enteroinvasive bacteria expressing the malaria epitope. Generation of a humoral response may be taken as an indication of a generalized immune response, other components of which, particularly cell-mediated immunity, may be important for protection against the malaria parasite. Test animals may include mice, rabbits, chimpanzees and eventually human subjects. Methods of introduction of the immunogen may include oral, intracerebral, intradermal, intramuscular, intraperitoneal, intravenous, subcutaneous, intranasal or any other standard routes of immunizations. The immune response of the test subjects can be analyzed by various approaches such as: the reactivity of the resultant immune serum to malaria antigens, as assayed by known techniques, e.g., enzyme linked immunosorbant assay (ELISA), immunoblots, radioimmunoprecipitations, etc.; or protection from Plasmodium infection and/or attenuation of malaria symptoms in immunized hosts.

5.6. FORMULATION OF A VACCINE

The purpose of this embodiment of the invention is to formulate a vaccine in which the immunogen is an attenuated enteroinvasive bacteria that expresses a malaria epitope so as to elicit a protective immune (humoral and/or cell-mediated) response against Plasmodium infections for the prevention of malaria. The bacteria of the vaccine comprise an attenuated enteroinvasive strain that is infectious for the host to be vaccinated. Such a live vaccine can be univalent or multivalent.

Multivalent vaccines can be prepared from a single or few recombinant attenuated enteroinvasive bacteria which express one or more Plasmodium-related epitopes. The vaccine may also include bacteria that express epitopes of organisms that cause other diseases, in addition to epitopes of malaria parasites. A single enteroinvasive bacteria can express more than one malarial epitope of the same or different antigens, and/or an epitope of a heterologous pathogen. The various epitopes may be expressed within the same protein (i.e., within a fusion protein), on separate proteins coded by the same or different expression vectors, or in different bacteria.

Many methods may be used to introduce the live vaccine formulations of the invention; these include but are not limited to oral, intradermal, intramuscular, intraperitoneal, intravenous, subcutaneous, and intranasal routes, including the natural route of infection of the parent wild-type bacterial strain.

In a specific embodiment, attenuated Salmonella expressing an epitope of a malarial circumsporozoite protein can be formulated as a vaccine.

5.6.1 VACCINATION STRATEGIES

Malaria vaccines can be directed at a specific stage in the life cycle of the parasite. In a particular embodiment, the vaccine can be directed at the sporozoite, the stage transmitted by mosquitoes, and which initiates infection in man.

An effective anti-sporozoite vaccine would have the intrinsic advantage of completely preventing infection. After being injected by the mosquito, sporozoites rapidly invade liver cells, where they develop into the stages which infect red blood cells and cause clinical illness. Thus, to completely block sporozoite infection of hepatocytes, high levels of antibodies against the sporozoite should be present.

In another embodiment, the vaccine formulation of the invention can be directed against an erythrocytic stage of the malaria parasite. This vaccine can be especially valuable, since antibodies against the sporozoite stage have no effect on asexual parasite stages which infect erythrocytes, and thus a single sporozoite which escapes the anti-sporozoite antibody-mediated immune response can still initiate a clinical case of malaria. Since mortality from malaria is related to the degree of parasitemia, even a blood-stage vaccine which produced less than complete immunity and reduced the numbers of infected red blood cells would be clinically useful.

Another specific embodiment of the invention involves the concept of transmission blocking immunity. Antibodies against the sexual (gametocyte) stage taken in with the blood meal can block fertilization of the parasite in the midgut of the mosquito, lyse gametes and zygotes, or block development of zygotes. In a particular embodiment, such a vaccine, which offers protection to populations as opposed to individuals, can be used as apart of a multivalent vaccine in malaria control programs.

Previous work with subunit vaccines demonstrated the need for effective malaria vaccine formulations. The CS gene of *P. berghei* has recently been cloned and sequenced (Weber et al., 1987, Experimental Parasitol. 63:295–300; see Section 7.1, infra). The repeat region of *P. berghei* contains four different octapeptides in a total of twelve units, as well as two dipeptides in a sixteen unit repeat. A peptide consisting of two repeats of the consensus octapeptide was coupled to keyhole limpet hemocyanin (KLH). Alternatively, the cloned gene containing approximately 70% of the actual coding sequence of the mature gene product including all of the repeat region was expressed in *E. coli*. The peptide, the recombinant protein, or gamma-irradiated sporozoites were used to immunize mice. Antibody titers measured by ELISA against peptide, the recombinant protein, and intact sporozoites, as well as CSP and ISI activity, were at least as high in the subunit vaccinated groups of mice as in the groups immunized with irradiated sporozoites. Significantly, only the irradiated sporozoite-immunized animals could be protected (90%) against high sporozoite challenge ($10^4$). Subunit vaccinated animals were protected only at the lowest sporozoite challenge dose (500). Protection was only partial and never exceeded 40% (Egan, J., et al., 1987, Science 236:453).

In recent studies, we have shown that transfer of T cells from sporozoite-immunized mice protected recipient animals, but mice receiving B cells or polyclonal immune sera were not protected, thus suggesting that cellular immunity is important.

The vaccine formulations of the present invention provide protective immunity against malaria, as a result of the expression of malaria epitopes in attenuated enteroinvasive bacteria, which allows the induction of cell-mediated immunity (CMI), in addition to humoral immunity We speculate that in the normal course of immunization with sporozoites, antibody prevents some but not all the sporozoites from reaching the liver. Sporozoites deposit CS protein on the surface of hepatocytes when they invade and developing exoerythrocytic forms (EE) express epitopes recognized by mAbs raised against sporozoites. These developing EE forms would be likely targets for natural killer cells and cytotoxic T cells or cytokine mediated responses. The failure of parenterally administered subunit CS vaccines to induce protective cellular responses may be a result of inappropriate antigen presentation in association with the MHC (major histocompatibility) molecule, or alternatively could indicate that epitopes critical to sporozoite induced immunity are not present on the CS protein. However, the latter explanation is unlikely, since the CS protein is the only known detectable surface antigen. The likelihood that targeting of the organism to a particular cell type and subsequent presentation of antigen in conjunction with the appropriate MHC molecule may be critical for induction of CMI is supported by the fact that protective immunization against sporozoite challenge requires the intravenous administration of intact, attenuated sporozoites. Neither intramuscular immunization nor use of the freeze-thawed or sonicated organisms induces significant protection (Spitalny, G. L. and Nussenzweig, R. S., 1972, Proc. Helm. Soc. Wash. 39:506).

A solution to this problem is to deliver the expressed CS protein (or other malarial antigen, or epitopes thereof) in an attenuated organism which can facilitate delivery to appropriate antigen-presenting cells, as provided by the vaccine formulations of the present invention. A preferred embodiment of the invention is the use of an avirulent non-pathogenic Salmonella oral vector delivery system. Use of this system can not only preclude some of the potential side effects associated with the use of other delivery vehicles such as vaccinia virus, but can also provide for convenient oral administration of malaria vaccines. This latter point is crucial for developing countries with limited health resources that are unable to support multiple administration of parenterally administered vaccines.

5.6.2. ORAL VACCINATION WITH ATTENUATED SALMONELLA

In a particular embodiment of the present invention, the concept of using attenuated species of Salmonella to deliver foreign antigens is based on the ability of Salmonella spp. to invade gut epithelial tissue and thereby gain access to mesenteric lymphoid tissue. In the mouse typhoid model, Takeuchi (1975, in Microbiology, American Society for Microbiology, Washington, D.C., pp. 174-181) has shown that following the attachment of *S. typhimurium* at the luminal brush border, bacteria invade the villus tip and become engulfed in pinocytized membrane vacuoles. Crossing the distal membrane of epithelial cells, the bacteria can disseminate throughout the reticuloendothelial system. When they reach the lamina propria, Salmonella cells cause an influx of macrophages which ingest the bacteria. Some cells escape phagocytosis and drain into mesenteric lymph nodes where they multiply. We postulate that stimulation of cell mediated responses is a consequence of invasion of the reticuloendothelial system. Thus, an innate feature of the attenuated oral vaccines of the invention is that they be able to invade the intestinal epithelium as can a pathogenic organism, but fail to cause active disease (e.g., because of a precisely defined genetic lesion), resulting in loss of pathogenicity. Oral malaria vaccines based on Salmonella have several advantages over vaccines now being developed. For example, with the appropriate genetic construction, the vector can mimic the sporozoite in surface presentation of the antigen and stimulate both cell-mediated and humoral immunity. Purification steps of a recombinant protein is not necessary, and the live attenuated Salmonella vaccine can be cheaply produced and conveniently administered (e.g., in a lyophilized form). In addition, the probability of adverse reactions based on available animal and human studies is low (Germanier, R., 1984, in Bacterial Vaccines, Academic Press, New York, pp. 137-165; Gilman, R. H., et al., 1977, J. Infect. Dis. 136:717; Levine, M. M., et al., 1983, Microbiol. Rev. 47:510; Smith, B. P., et al., 1984, Am. J. Vet. Res. 45:2231; Smith, B. P., et al., 1984, Am. J. Vet. Res. 45:59; Wray, C., et al., 1982, Develop. Biol. Standard 53:41; Wray, C., et al., 1977, J. Hyg. Camb. 79:17).

6. EXAMPLE: MATERIALS AND METHODS

6.1. CONDITIONS FOR RESTRICTION ENZYME DIGESTIONS

Restriction endonucleases were purchased from BRL (Bethesda Research Laboratories, Bethesda, Md.), IBI (International Biotechnologies, Inc., New Haven, Conn.), New England Biolabs (Beverly, Mass.), or U.S. Biochemical Corporation (Cleveland, Ohio).

Restriction enzyme digestions were carried out by suspending DNA in the appropriate restriction buffer, adding restriction endonuclease, and incubating for an appropriate period of time to ensure complete digestion. One unit of enzyme is defined as the amount required to completely digest 1.0 ug of phage lambda DNA in 1 hour in a total reaction mixture of 10 ul volume. Buffers used with the various enzymes are listed below:

Low salt buffer used for ClaI, HpaI, HpaII, and KpnI digestions consisted of: 10 mM Tris-Cl (pH 8.0), 10 mM $MgCl_2$, and 10 mM dithiothreitol (DTT).

Medium salt buffer used for AluI, AvaI, SspI, TaqI, XmaI, and XmnI digestions consisted of: 50 mM Tris-Cl (pH 8.0), 10 mM $MgCl_2$, 50 mM NaCl, and 10 mM DTT.

High salt buffer used for BamHI, EcoRI, EcoRV, NcoI, and SalI digestions consisted of: 50 mM Tris-Cl (pH 8.0), 10 mM $MgCl_2$, 150 mM NaCl, and 10 mM DTT.

The buffer used for SmaI digestions consisted of: 10 mM Tri-Cl (pH 8.0), 20 mM KCl, 10 mM $MgCl_2$, and 10 mM DTT.

All restriction digestions were carried out at 37° C. except TaqI, which was carried out at 60° C.

6.2. GEL PURIFICATION OF DNA FRAGMENTS

After restriction enzyme digestions, DNA fragments of sizes were separated and purified by gel electrophoresis in agarose using 0.1M Tris-Borate buffer (pH 8.0) containing 2 mM EDTA at 10 volts/cm. Agarose concentrations varied from 0.8% to 1.5% depending on the size of the fragments to be recovered. DNA bands were visualized by ethidium bromide fluorescence. DNA was recovered by electroelution of the chosen DNA fragment onto NA45 paper (Schleicher and Schuell, Keene, N.H.), followed by incubation of the NA45 paper at 68°

C. in a buffer consisting of 10 mM Tris (pH 8.0), 1 mM EDTA and 1M NaCl.

6.3 SYNTHESIS AND PURIFICATION OF OLIGONUCLEOTIDES

Oligonucleotides were synthesized on the 0.2 micromole scale, on an Applied Biosystems Inc. model 380B DNA synthesizer, using beta-cyanoethyl-phosphoramidite chemistry (Sinha, N. D., et al., 1984, Nucl. Acids Res. 12:4539-4544).

Oligonucleotides were purified by electrophoresis in a 0.4 mm thick 8% polyacrylamide gel in TBE buffer (0.01M Tris-borate, pH 8.2, 1 mM EDTA), run at approximately 1600 volts with a constant power of 75 watts. Oligonucleotide bands were visualized by negative shadowing over a PEI (polyethylene-imine) thin-layer chromatography plate under ultraviolet light, and the band of full length product was excised from the gel. The synthetic oligonucleotide was eluted in 0.3M sodium acetate pH 5.5, and was precipitated by the addition of two volumes of 100% ethanol, chilled to $-20°$ C., and centrifuged at $14,000 \times g$. The DNA pellets were dried under vacuum and dissolved in TE buffer (10 mM TrisCl, pH 7.4, 1 mM EDTA).

Phosphate groups were incorporated at the 5, terminus of the synthetic oligonucleotides using T4 polynucleotide kinase (New England Biolabs, Beverly, Mass.). One microgram amounts of purified oligonucleotide were dissolved in 25 microliters of kinase buffer consisting of 70 mM Tris-Cl (pH 7.6), 10 mM $MgCl_2$, 5 mM DTT, with 1 mM adenosine triphosphate (ATP). This solution was incubated with 20 units T4 polynucleotide kinase for 30 minutes at 37° C.

Annealing of complementary strands was achieved by mixing the kinased strands and heating to 60° C. for 1 hour and cooling to room temperature. Annealed strands were used directly in ligation procedures.

6.4. CREATION OF FLUSH ENDS IN DNA FRAGMENTS

To create blunt ends for ligation, DNA termini with 5, overhangs resulting from digestion with restriction enzymes, were either filled-out by the action of the large fragment of DNA polymerase I (Klenow fragment), or removed by the action of mung bean nuclease. For filling-out with Klenow enzyme, approximately 1 microgram of DNA was treated with 1 unit of enzyme in 25 microliters of a buffer consisting of 50 mM Tris-Cl (pH 7.0), 10 mM $MgSO_4$, 0.1 mM dithiothreitol, and 50 ug bovine serum albumin per ml. A combination of deoxynucleotide triphosphates (dGTP, dCTP, dATP, dTTP) at a final concentration of 100 micromolar was also included. For digestion with mung bean nuclease, approximately 1 microgram of DNA was incubated with 1 unit of mung bean nuclease in 20 microliters in a buffer consisting of 50 mM sodium acetate (pH 5.0), 30 mM NaCl, and 1 mM $ZnSO_4$. Incubation was at 30° C. for 0.5 to 1 hour. mung bean nuclease and Klenow enzyme were obtained from New England Biolabs, Beverly, Mass.).

6.5. DNA LIGATION

All ligations were accomplished using T4 DNA ligase. T4 DNA ligase was purchased from BRL (Bethesda, Md.), U.S. Biochemical Corporation (Cleveland, Ohio), or Boehringer (Indianapolis, Ind.). One unit (U) of T4 DNA ligase is defined as the amount required to yield 50% ligation of HindIII fragments of bacteriophage lambda DNA in 30 minutes at 60° C. in 20 ul volume ligase buffer at a 5'-DNA termini concentration of 0.12 uM (300 ug/ml). DNA ligations were performed in ligase buffer consisting of 50 mM Tris-Cl (pH 7.5), 10 mM $MgCl_2$, 10 mM DTT, and 1 mM ATP. Normally, DNA concentration ranged from 20-30 ug/ml. T4 DNA ligase was added at a ratio of 1 U per 20 ul reaction volume. Incubations were carried out for 18-24 hours. Temperatures used were 15° C. for cohesive end ligations, and 22° C. for blunt end ligations. If sufficient material was available, ligations were checked by analyzing a portion of the reaction mixture by agarose gel electrophoresis.

6.6. TRANSFORMATION OF PLASMID DNA

Plasmid constructions resulting from the ligation of fragments of circumsporozoite genes (or synthetic oligonucleotides related to such gene sequences) to cloning or expression vectors, were inserted into common laboratory strains of *Escherichia coli* by transformation techniques (for details, see Maniatis et al., 1982, Molecular Cloning, A Laboratory Manual, Cold Spring Harbor Laboratory, Cold Spring Harbor, N.Y.). Plasmid constructions were isolated and characterized first in *E. coli*, before transferring to Salmonella spp., because of the high transformation frequencies of *E. coli* K-12 relative to those of *S. typhimurium*. Plasmids were transferred into *S. typhimurium* LT-2 LB5010, a strain lacking several of the restriction systems known to exist in various Salmonella species and also containing a mutation in galE resulting in higher transformation frequencies (for a description of restriction systems of *Salmonella typhimurium*, see Bullas et al., 1980, J. Bacteriol. 141:275). Plasmids transformed into LB5110 were characterized for expression of the desired CS protein construct and, after verification by restriction enzyme analysis, plasmids were inserted into attenuated Salmonella by transduction techniques. LB5010 containing desired plasmid was grown in Luria broth (LB) to a density of $3\times10^8$ cells/ml, at which point D-galactose (to a final concentration of 1%) was added to the growth medium to induce synthesis of lipopolysaccharide (LPS). Following 1.5 hours of growth in the presence of D-galactose, bacteriophage P22 HT 105/1 int was added to the culture to a multiplicity of infection of one. Following adsorption of the phage, cells were immobilized in LB containing 0.7% agar. Phage were harvested and used to transduce plasmids into any attenuated Salmonella containing LPS as a component of the receptor for the transducing phage P22.

6.7. SYNTHESIS AND PURIFICATION OF CS IMMUNODOMINANT PEPTIDES

To demonstrate antigenicity or immunogenicity of subunit vaccines when compared to live attenuated Salmonella carrying CS proteins, two synthetic peptides, one representing two repeat units of circumsporozoite (CS) protein from *Plasmodium berghi* (DPAPPNAN; D-16-N) and the second representing 3 repeat units of CS from *Plasmodium falciparum* [(NANP)3] were synthesized by the solid phase method on an automatic peptide synthesizer (Applied Biosystem Model 430A). Synthetic peptides also served as capture antigens in ELISA assays.

The peptide chain was assembled on an insoluble polystyrene resin to which the carboxy terminal amino acid was attached through a special organic spacer known as "PAM" linker. Amino acids, protected with t-butyloxycarbonyl (BOC), were coupled to the free alpha-amino groups on the growing peptide chain in an aprotic, polar solvent. Premature chain termination and peptide self-aggregation on the resin support was minimized by keeping the peptide chain dissolved in dimethylformamide during the coupling steps. The coupling reaction was monitored by a quantitative ninhydrin procedure which measures residual free alpha-amino groups on the peptide resin. All reactive side chains of individual t-BOC amino acids were protected with benzyl based protecting groups.

The completed peptides were cleaved from the resin, and all side-chain protecting groups were removed by anhydrous hydrofluoric acid (HF) treatment. After strong acid cleavage and deprotection, the reaction mixture was washed well with anhydrous ether and dissolved in dilute acetic acid. The resin was filtered, and the aqueous solution was collected and lyophilized to yield the crude peptide preparation.

The homogeneity of the peptide obtained from HF cleavage was evaluated on a micropore HPLC (high performance liquid chromatography) system (Applied Biosystems Model 130A separation system) using a reverse phase column. If HPLC analysis revealed a single major peak, no further purification was performed. If the HPLC chromatogram showed a mixture of peaks, preparative HPLC was performed to separate peaks. The purified product was subjected to acid hydrolysis for amino acid analysis to verify the amino acid composition. The synthetic peptides were sequenced by automated Edman degradation with a protein sequenator (Applied Biosystems Model 477A) equipped with a fully automatic on-line phenylthiohydantoin (PTH) analyzer (Model 120A).

6.8. PEPTIDE-KEYHOLE LIMPET HEMOCYANIN CONJUGATION PROCEDURE

Synthetic peptides were coupled to keyhole limpet hemocyanin (KLH) by glutaraldehyde cross-linking. KLH (obtained from Calbiochem, San Diego, Calif.) was dialysed against 0.1M sodium bicarbonate buffer (pH 9.6) and adjusted to 1 mg/ml in the same buffer. Peptides were made in water or 0.1M sodium bicarbonate buffer at 4 mg/ml. Equal volumes of protein and peptide solutions were mixed and rotated for 1 hour at room temperature. Four microliters of 25% aqueous solution of glutaraldehyde was added and rotated for another 24 hours, followed by another 25 microliters of 25% glutaraldehyde and rotation for 72 hours at room temperature. The conjugated material was dialysed against phosphate-buffered saline for 24 hours. Peptide-KLH conjugates were tested in ELISA, as previously described (Egan et al., 1984, Science 236:453). Initially, plates were coated with different concentrations of conjugates, and the concentration that reacted well with the appropriate monoclonal antibodies was selected for coating plates in all future experiments.

6.9. POLYACRYLAMIDE GEL ELECTROPHORESIS

To analyze proteins by polyacrylamide gel electrophoresis (PAGE), cells from 1 ml of culture were washed and resuspended in 100 microliters of a lysing buffer (0.2M Tris-HCl buffer containing 5% SDS, 0.025% bromophenol blue, 0.1 to 1M 2-mercaptoethanol, and 20% glycerol), and heated for 5 minutes at 100° C. Most analyses were performed using the Bio-Rad Mini Protean Gel system (Redmond, Calif.). Gels were 1.5 mm thick, and the separating gel contained 15% acrylamide, with an acrylamide to bis-acrylamide ratio of 30:0.8, 0.375 M Tris-HCl (pH 8.8), and 0.1% sodium dodecyl sulfate (SDS). The stacking gel contained 4.8% acrylamide with the same 30:0.8 ratio of acrylamide to bis-acrylamide, 125 mM Tris-HCl (pH 7.0), and 0.1% SDS.

Ten to fifteen microliters of samples (containing 5–20 micrograms protein) were applied to each lane. Following electrophoresis, gels were stained for at least 1 hour with 0.125% Coomassie blue in ethanol:acetic acid:water (5:1:5), then destained in the same solvent system without the dye. Pre-stained low molecular weight standards (ovalbumin, 43,000; alpha-chymotrypsinogen, 25,700; B-lactoglobulin, 18,400; lysozyme, 14,300; bovine trypsin inhibitor, 6,200; insulin, 2,300 and 3,400; obtained from Bethesda Research Laboratories, Gaithersburg, Md.) were also subjected to electrophoresis to assist in the determination of the relative molecular weight of the observed proteins. An unstained duplicate gel without staining was used for western analysis.

6.10. WESTERN BLOT AND ISOELECTRIC FOCUSSING ANALYSIS

Samples separated by PAGE were transferred electrophoretically onto nitrocellulose membranes in a Hoeffer Transphor apparatus at 0.45 milliamps for 90 minutes in 25 mM Tris, 384 mM glycine (pH 8.8) at room temperature. Once protein transfer was complete, nitrocellulose membranes were soaked in BLOTTO (5% non-fat dry milk in phosphate-buffered saline) at 37° C. for 1 hour. Membranes were probed with a pre-determined concentration of monoclonal antibodies against P. berghei or P. falciparum CS protein repeat regions for 1 hour at 37° C. and washed with BLOTTO for 20 minutes at 37° C. Bound antibodies were detected by incubation with horseradish peroxidase-conjugated goat anti-mouse IgG (Kirkegaard and Perry, MD) at 1:250 dilution in BLOTTO for 1 hour at 37° C. Blots were washed three times with PBS, and developed with PBS containing 0.01% hydrogen peroxide, 0.06% 4-chloro-1 napthol (Sigma Chemical Co., Mo.), in methanol for 20 minutes at room temperature. The reaction was stopped by transferring the filters to distilled water. The filters were dried by blotting.

For isoelectric focussing of proteins in polyacrylamide gels, approximately 10–50 micrograms of total cell proteins were applied to the gel. Cell extracts were prepared by harvesting bacteria in the logarithmic phase of growth, and concentrating them fifty-fold by centrifugation and resuspension in 0.5 ml of 10 mM TrisHCl, pH 8.0, containing 1 mM EDTA and 20 ug lysozyme per ml. After digestion with lysozyme, extracts were subjected to sonication. Whole cells and cellular debris were removed by centrifugation at 12,000×g, and the supernatant samples, in a volume of 10–50 microliters, were applied to an isoelectric focussing gel in a sample buffer consisting of 10% v/v glycerol, 2% carrier ampholytes (pH 3–10) and 0.001% methyl red. Focussing gels consisted of 7.5% acrylamide containing 2% ampholytes C (pH 3–10; purchased from BioRad, Richmond, Calif.). Focussing of proteins was carried out over a 4–5 hour period at 2000 V. Focussed proteins were transferred to nitrocellulose by electroblotting, followed by visualisation with monoclonal antibody to the CS protein repeat region as described supra for the western blot technique.

6.11. COLONY BLOT SCREENS FOR CIRCUMSPOROZOITE PROTEIN EXPRESSION IN E. COLI

E. coli transformant colonies were screened for expression of the immunodominant CS epitope by lysing cells retained on nitrocellulose filters by exposure to chloroform vapors for a period of 20 minutes. Lysed colonies were washed off the nitrocellulose filter by immersing the filters in a blocking solution consisting of 50 mM Tris-Cl, pH 8.0, containing 0.15M NaCl, 5 grams of Carnation instant dried milk (BLOTTO) per 100 ml of solution, 1 microgram boiled RNase per ml, 1 microgram DNase per ml, and 200 micrograms egg white lysozyme per ml. Filters were washed further in BLOTTO, and monoclonal antibody 3.28 (Egan et al., 1987, Science 236:453), capable of recognizing the immunodominant repeated epitope of P. berghei, or a mixture of two or more monoclonal antibodies, mAb 4D9.1P or mAb 565, reacting with the repeat epitope of P. falciparum (Dame et al., 1984, Science 225:593), was added to a concentration of 10-100 nanograms per ml of blocking solution. Filters were incubated for 1 hour at 37° C., followed by washing in BLOTTO. The bound antibody was amplified by addition of rabbit anti-mouse IgG antibody, and incubation for another hour at 37° C. The signal was developed by incubation with goat anti-rabbit IgG coupled to horseradish peroxidase. Horseradish peroxidase was visualized by reaction in the presence of 0.06% 4-chloro01-napthol (w/v) and 0.15% hydrogen peroxide (v/v).

6.12. ENZYME-LINKED IMMUNOABSORBENT ASSAY FOR SERUM ANTI-CS AND ANTI-LT-B ANTIBODIES

To measure serum antibodies, 96 well polystyrene plates (NUNC) were coated with 1 ug/ml of LT-B or 5 ug/ml of D-16-N-KLH, a synthetic peptide representing two repeat units of Plasmodium berghei CS protein coupled to KLH by glutaraldehyde cross-linking. Each well received 0.1 ml of antigen in 0.1M carbonate/bicarbonate buffer (pH 9.6). Plates were incubated at 37° C. in a humidified incubator for 18 hours, before being washed 3 times with PBS containing 0.05% Tween 20 (PBS-T) and blocked with 0.1% gelatin in PBS for 60 minutes at room temperature. Plates were washed 3 times with PBS-T, and serial dilutions of sera were added and incubated for 90 minutes at room temperature. Goat anti-LT-B or mAb 3.28, or pools of mAb 4D9.1P and mAb 565, were used as positive controls in assays. Plates were washed as before, and pre-optimized concentrations of alkaline phosphatase-conjugated rabbit anti-goat immunoglobulin (at a 1:3000 serum dilution; Tago, Burlingame, Calif.), and goat anti-mouse immunoglobulin (at a 1:5000 serum dilution; Tago, Burlingame, CA) were added to appropriate wells and incubated for 60 minutes at room temperature. Plates were washed again, and 100 microliters of substrate solution (p-nitrophenyl phosphate at 1 mg/ml in diethanolamine buffer, pH 9.6) was added to each well. The signals were developed for 60 minutes at room temperature, and read in a Bio-Tek automatic ELISA reader using dual wavelengths at 410 nm and 690 nm, blanking on air.

6.13. CHALLENGE OF MICE WITH LIVE SPOROZOITES

Sporozoites of Plasmodium berghei were obtained from salivary glands of infected female Anopheles mosquitoes. The salivary glands were dissected out and collected in ice-cold tissue culture medium M199 supplemented with 10% normal mouse serum. The glands were gently triturated in a loose-fitting glass grinder. Sporozoites were separated from mosquito tissue debris by centrifuging triturated glands at 500 rpm in a Sorvall SS34 rotor for 3 minutes at 4°C and collecting parasite-containing supernatant. For maximum yield, the extraction was repeated twice. The concentration of sporozoites was determined by counting the parasites in a hemocytometer.

Seven to 14 days after the final vaccination, animals were divided into sub-groups and challenged with a low dose (500) or high dose (2000) of sporozoites of Plasmodium berghei. Starting from day 3 after challenge, mice were examined daily for mortality and for detectable parasitemia in Giemsa-stained blood smears. All patent infections usually appeared within 10 days after challenge.

7 EXAMPLE: EXPRESSION VECTORS FOR PLASMODIUM CIRCUMSPOROZOITE PROTEIN GENES

7.1. DNA SEQUENCE OF THE GENE FOR THE pi P. BERGHEI CIRCUMSPOROZOITE PROTEIN

The gene encoding approximately 75% of the carboxy-terminal portion of the circumsporozoite protein of P. berghei was obtained as an 1140 base pair EcoRI restriction fragment in the plasmid vector pUC8 (Veira, J. and Messing, J., 1982, Gene 19:259). The DNA sequence of the fragment has been previously determined (Weber et al., 1987, Experimental Parasitol. 63:295), and is depicted in FIG. 1, with the deduced amino acid sequence listed in FIG. 2. In addition to the sequence shown in FIG. 1, an EcoRI-TaqI oligonucleotide linker was used during the initial cloning and is contained within the EcoRI restriction fragment. This adapter, or linker region, contains nucleotide sequences which comprise recognition sites for restriction endonuclease cleavage. These restriction enzyme sites can be used as convenient cleavage sites for subcloning the gene sequence into expression vectors. The sequence of the adapter region is as shown (the adapter sequences are underlined):

circumsporozoite protein gene

| TaqI | NruI | XmnI |
|---|---|---|
| 5' AATTCGAACCCCTTCG | CGA ... TAT | CGCGAAGGGGTTCGAATT 3' |
| XmnI | NruI | TaqI |

7.2. CONSTRUCTION OF PLASMID pPX100, EXPRESSING LT-B UNDER THE CONTROL OF THE lac OPERON Plasmid pJC217 encodes 100 amino acids of mature *E. coli* enterotoxin subunit B, LT-B, and also encodes a 20 amino acid amino-terminal signal sequence which is cleaved from the mature molecule. Plasmid pJC217 was obtained by insertion of approximately 800 base pairs of LT-B DNA (the sequence of which is shown in FIG. 3), from a genomic fragment of enterotoxigenic *E. coli* H10407, into the HindIII site of plasmid vector pUC8.

To obtain an expression vector in which fusions of the circumsporozoite protein of *P. berghei* with various regions of LT-B can be created, plasmid pJC217 was modified to delete extraneous restriction sites associated with the polylinker region of pUC8. By digesting pJC217 with the restriction enzyme EcoRI and religating the reaction products, a deletion of 180 base pairs of DNA including the DNA specifying the restriction sites of the polylinker region was obtained, resulting in plasmid vector pPX100 (FIG. 4). In this configuration, LT-B is controlled by the lac operon promoter of *E. coli*. After transfer of the plasmid into a suitable bacterial host, e.g., *E. coli* JM103 (Clements et al., 1984, Infect. Immun. 46:564), LT-B transcription can be induced by inclusion of isopropyl-thio-beta-D-galactoside (IPTG) in the growth medium of the recombinant bacteria. The DNA sequence of LT-B is depicted in FIG. 3; restriction enzyme sites useful in creating fusion protein molecules are indicated.

7.3. EXPRESSION OF THE CIRCUMSPOROZOITE PROTEIN OF *P. BERGHEI* IN *E. COLI* AS A FUSION PROTEIN WITH BETA-GALACTOSIDASE

To obtain expression of the circumsporozoite protein gene in *E. coli*, plasmid pUC8 containing the 1.1 kilobase pair EcoRI CS fragment was digested with either NruI or XmnI under standard conditions for those enzymes. A 670 base pair XmnI fragment was purified by electrophoresis through a 1% agarose gel and eluted from agarose by electrophoresis onto NA45 paper (Schleicher and Schuell, Keene, N.H.). The DNA fragment was eluted off of the NA45 paper by incubating the paper in a 250 microliter volume of 10 mM Tris hydrochloride buffer, pH 8.0, containing 1M NaCl and 5 mM EDTA. DNA was precipitated from the NaCl buffer by addition of two volumes of ethanol, and the DNA pellet was obtained by centrifugation at 12,000×g for 5 minutes at 4° C. The 1.1 kilobase pair NruI fragment was purified in the same fashion. The XmnI and NruI DNA fragments were each redissolved in a sufficient volume of 10 mM Tris hydrochloride containing 10 mM EDTA to yield a final concentration of approximately 1 microgram per microliter. Plasmid vector pUC8 was digested with HincII and mixed either the with purified XmnI or the NruI fragment, and the DNA ends were joined with T4 DNA ligase. The ligation products were transformed into *E. coli* JM103, with selection for resistance to ampicillin.

7.3.1. DETECTION OF TRANSFORMANT COLONIES EXPRESSING THE REPEATED EPITOPE OF THE CIRCUMSPOROZOITE PROTEIN

Transformant bacterial colonies reacting with mAb 3.28, an antibody which recognizes the immunodominant repeated epitope of *P. berghei* CS, were detected by the colony blot method described in Section 6.11, following induction of lac operon expression by transfer of the colonies to an LB agar plate containing 1 mM IPTG.

After transformation with the plasmid resulting from religation of pUC8 restricted by the enzyme HincII in the presence of either the 1.1 kilobase pair NruI CS fragment or the 670 base pair XmnI CS fragment, as described above, approximately 10% of the resulting transformants demonstrated significant color development when reacted with mAb 3.28. Among the reactive colonies from each ligation, several candidates were retained and analyzed further. Plasmids isolated from each candidate colony were subjected to restriction enzyme analysis to confirm the presence of characteristic cleavage sites. Plasmid pPX1512 results from the linkage of the 670 base pair XmnI fragment in frame with the first eleven amino acids encoded by the polylinker region of pUC8, and reads in-frame through the 223 amino acids encoded by the DNA of the XmnI fragment through the following sixty-eight amino acids of the beta-galactosidase peptide, termed the lac alpha peptide, encoded in the pUC8 vector. Plasmid pPX1514 results from the linkage of the 1.1 kilobase pair NruI fragment into the HincII site of pUC8, and contains a fusion of the first eleven amino acids of the polylinker region to 272 amino acids of the circumsporozoite protein. The translated protein of pPX1514 terminates with the translation termination codon TAA supplied in the circumsporozoite protein sequence.

7.4. FUSION OF THE *P. BERGHEI* CIRCUMSPOROZOITE PROTEIN TO THE CARRIER POLYPEPTIDE LT-B

The circumsporozoite gene of *P. berghei* was linked to the gene for the B subunit of *E. coli* enterotoxin, LT-B, at three separate loci within the gene sequence. As diagrammed in FIGS. 5 and 6, pPX100 was cut with three separate restriction enzymes by standard techniques, and the resulting cohesive ends were modified so that blunt-end ligation of either the XmnI or the NruI fragment containing the repeat regions of the circumsporozoite gene would result in in-frame fusion of the CS gene with regions of the LT-B gene contained in pPX100. First, pPX100 was cut with ClaI and the cohesive ends "filled- out" by the action of the Klenow fragment of DNA polymerase I in the presence of dCTP and dGTP. When the 670 base pair XmnI CS fragment was ligated to the modified ClaI site, an LT-B fusion protein resulted. This protein, as encoded in pPX1515, comprises the first 30 amino acids of mature LT-B fused to 223 amino acids of the CS gene, followed by an out-of-frame readthrough of twenty-eight amino acids derived from LT-B DNA downstream from the ClaI site. When the 1.1 kilobase pair NruI fragment was ligated to the modified ClaI site, a protein resulted in which the first thirty amino acids of mature LT-B were fused with 272 amino acids of the CS gene, with translation terminating with the termination codon of the CS gene.

Equivalently, pPX100 was digested with XmaI and treated further with mung bean nuclease to remove the overhanging 5' terminus. The 1.1 kilobase pair NruI CS fragment was ligated to this modified site, yielding plasmid pPX1523. The resulting fusion protein contained sixty amino acids of mature LT-B linked to 223 amino acids of the CS gene, followed by an out-of-frame readthrough of four amino acids derived from LT-B DNA. To fuse the CS protein sequences to the carboxy-terminal amino acid of mature LT-B, pPX100 was digested with the restriction enzyme SpeI. The resulting cohesive termini were partially filled in by the action of the Klenow enzyme of DNA polymerase I in the presence of dCTP, and the remaining overhang was digested with mung bean nuclease. Blunt-end ligation of either the 1.1 kilobase pair NruI or the 670 base pair XmnI CS fragment resulted in the fusion proteins depicted in FIG. 6. Plasmid pPX1525 encodes a LT-B/CS fusion protein in which 100 amino acids of mature LT-B is linked to 223 amino acids of the CS protein, followed by forty amino acids read out-of-frame, which are derived from DNA present in the LT-B clone (outside the coding region of LT-B).

7.5. MANIPULATION OF TRANSCRIPTIONAL PROMOTER AND TRANSLATION INITIATION SIGNALS TO OBTAIN HIGHER LEVELS OF LT-B/CS FUSION PROTEIN EXPRESSION

Increased expression of LT-B CS fusion proteins was obtained by inserting the fused gene sequences directly downstream from either of two strong promoter sequences known to function well in *E. coli*. The tac promoter results from the fusion of the −35 region of the trp operon promoter with the −10 region of the UV5 lac promoter (DeBoer, H., et al., 1982, in Promoter Structure and Function, Rodriguez, R. L. and Chamberlain, M. J., eds., Praeger Publishing, New York). The tac promoter is controlled by the lacI gene product, a repressor which binds to the lac region of the DNA and inhibits transcription by RNA polymerase. In the presence of the lacI gene product, gene expression can be induced by IPTG present in the bacterial growth medium. The $P_L$ promoter of coliphage lambda controls leftward transcription of mRNA during lytic growth of the virus in its natural host, *E. coli* (Shimatake, H. and Rosenberg, M., 1981, Nature 292:128). The PL promoter is repressed during lysogeny by the cI gene repressor protein. When either the tac promoter or the PL promoter is used to drive gene transcription in a closely related enteric host bacterium such as Salmonella spp., gene transcription is constitutive unless appropriate repressor functions are also introduced. Gene transcription results in constitutive synthesis of proteins encoded by DNA downstream from the promoter sequences. Synthesis of antigenic proteins in a Salmonella spp. host, such as the LT-B/CS fusion proteins described in Section 7.4, results in constant presentation of the antigenic molecules during the period of time the attenuated bacteria can replicate within the animal host, either in the experimental test animal such as the mouse, or in humans. A high level of specific protein synthesis relative to endogenous bacterial host proteins favors host immune response to the recombinant DNA-derived proteins.

To demonstrate increased synthesis of equivalent proteins expressed in Salmonella spp., each of the family of LT-B/CS fusion proteins diagrammed in FIG. 6 was inserted directly downstream from either the tac promoter (FIG. 7) or the $P_L$ promoter (FIG. 8). The translation initiation signals derived from LT-B are retained within the EcoRI-HindIII fragments encoding the LT-B/CS fusion proteins and include a ribosome binding site (S/D sequence) and the translation start codon of LT-B at the 5′ terminus of the gene sequence (FIG. 6). Plasmid vector pKK223 (purchased from Pharmacia Molecular Biologicals, Piscataway, N.J.) contains the tac promoter, but lacks suitable translation start sequences downstream from the promoter. Plasmid pKK223 was digested with restriction enzymes EcoRI and HindIII. The plasmid vector fragment was purified by electrophoresis through agarose and was ligated to purified EcoRI-HindIII restriction fragments derived from either pPX1515, pPX1523, or pPX1525. Transformants obtained in *E. coli* JM103 were screened for production of proteins reactive to the specific anti-CS monoclonal antibody, mAb 3.28, after transfer of bacterial colonies to LB agar containing 1 mM IPTG. Reactive colonies were purified, and DNA isolated from them was screened further by restriction enzyme analysis. Those colonies showing the expected DNA restriction patterns were retained. As diagrammed in FIG. 7, plasmid pPX1528 was obtained in this fashion.

To obtain expression of an equivalent family of fusion proteins controlled by the $P_L$ promoter of coliphage lambda, the EcoRI-HindIII restriction fragments derived from pPX1515, pPX1523, and pPX1525 were treated with the Klenow fragment of DNA polymerase I in the presence of dATP, dTTP, dCTP, and dGTP, to create blunt ends at both the EcoRI end and the HindIII end of the fragments (FIG. 8). By ligating the blunt-ended fragments into the HpaI site of plasmid vector $pP_L$-lambda (Pharmacia), a series of plasmids encoding fusion proteins controlled by the $P_L$ promoter was obtained by transforming *E. coli* N99 cI+. Plasmid pPX1601 was derived from a fragment of pPX1515, ligated into expression vector $pP_L$-lambda (FIG. 8). Transformants were screened in *E. coli* for the presence of unique restriction fragments. Suitable candidates were then transformed into *E. coli* strain N4830, which is lysogenic for a defective bacteriophage lambda harboring a temperature-sensitive repressor allele, cI857. In this *E. coli* host strain, genes controlled by the lambda $P_L$ promoter are inducible by switching the temperature of the growth medium from 32° C. to 42° C. As depicted in FIG. 8, in this configuration, translation initiation signals are supplied by the S/D sequence and translation initiation codon (ATG) derived from LT-B. The vector also encodes part of the bacteriophage lambda N gene, whose transcription is controlled by the $P_L$ promoter. By inserting the blunt ended EcoRI-HindIII fragment of the LT-B/CS fusion proteins in the HpaI site, the N gene terminates with the TGA codon immediately after the S/D sequence as shown in FIG. 8.

7.6. CONSTRUCTION OF EXPRESSION VECTORS TO PROMOTE TRANSCRIPTION FROM THE LAMBDA $P_L$ PROMOTER OF GENES ENCODING CIRCUMSPOROZOITE PROTEINS

To provide suitable translation initiation signals downstream from the $P_L$ promoter, an oligonucleotide was designed to be inserted into the HpaI site of $pP_L$ lambda. This oligonucleotide consists of 53 base pairs; the sense strand is diagrammed in FIG. 9. The synthetic oligonucleotide is designed so that translation of the N gene terminates at the TAA immediately upstream from the S/D sequence. In addition, the presence of KpnI and NcoI sites bracketing the S/D sequence allows for the facile insertion of short synthetic oligonucleotides in order to randomize the base sequence around the S/D sequence and obtain increased translation efficiency. In addition, the oligonucleotide specifies three restriction sites, namely, NcoI, StuI, and EcoRV, which allow for insertion of heterologous sequences in all three reading frames. The NcoI site encompasses the required ATG initiation codon, which can be supplied as a blunt end by filling out the cohesive NcoI end with Klenow enzyme in the presence of all four deoxynucleotides. Moreover, the sequence encodes translation stop codons in all three reading frames, so that predictable termini for fusion proteins are obtained.

Plasmid pPX1529 was obtained by ligating vector pPX1600 (after treatment with NcoI and filling out the cohesive ends with Klenow enzyme) to the 670 base pair XmnI fragment encoding the *P. berghei* CS protein repeat epitope and Regions I and II (FIG. 10). In addition, by treating the 670 base pair XmnI fragment with NruI, followed by purification and ligation of the resulting DNA fragment into the filled NcoI site of pPX1600, a plasmid (pPX1531) was obtained in which the codon for arginine (CGA), derived from the proper *P. berghei* CS DNA sequence, was fused directly to an amino terminal methionine. Thus, no extraneous amino acids resulting from the translation of linker DNA, other than the initial methionine, was obtained. A seven amino acid carboxy terminal addition was obtained in this fusion, resulting from the translation of codons derived from the synthetic insert of pPX1600.

7.7. INSERTION OF EPITOPES OF *P. FALCIPARUM* AND *P. BERGHEI* INTO THE pPX1600 EXPRESSION VECTOR

To express the CS repeat regions of either the rodent malaria parasite *P. berghei* or the human malaria parasite *P. falciparum* at appropriately high levels in *E. coli* and Salmonella spp., synthetic complementary oligonucleotide strands were designed as diagrammed in FIG. 11. The oligonucleotide encoding the *P. falciparum* repeat region was based on the consensus sequence ASN ALA ASN PRO (NANP) repeated four times. In addition, the oligonucleotide was designed so that asymmetrical HinfI cohesive termini were formed at each end. By treating the annealed complementary strands with T4 polynucleotide kinase and T4 DNA ligase, head to tail polymerization of the repeated epitope was achieved. Creating blunt ends from the resulting single HinfI cohesive ends and ligating the fragment into the blunt-ended NcoI site of pPX1600 resulted in a series of transformants of *E. coli* strain N99 cI⁻ containing the *P. falciparum* CS repeat epitope. (This strain of *E. coli* expresses the cI⁺ temperature-insensitive wild-type lambda repressor, and is lysogenic for bacteriophage lambda.) By screening the transformants with appropriate restriction enzymes, clones having from one (monomer) to four (tetramer) copies of the *P. falciparum* oligonucleotides in the correct orientation with respect to the P$_L$ promoter were obtained. These plasmids were transformed into the *E. coli* expression host N4830 (cI857), where expression of the epitope induced by temperature shift was confirmed by colony blot analysis and western blot analysis.

Concurrently, an oligonucleotide encoding two repeats of the *P. berghei* consensus octapeptide epitope (ASP PRO ALA PRO PRO ASN ALA ASN: DPAPPNAN) was synthesized. As described supra, two complementary strands were designed so that head to tail polymerization could occur upon ligation of annealed strands following treatment with T4 polynucleotide kinase and T4 DNA ligase. Ligated oligonucleotides were treated with Klenow enzyme in the presence of deoxynucleotides and the resulting blunt-ended family of fragments were ligated to the filled-out NcoI site of pPX1600. Transformant colonies were selected in *E. coli* N99 (cI+) and analyzed by restriction enzyme digestion. Monomeric to tetrameric inserts were isolated and characterized further for expression of the immunodominant epitope by screening plasmids for induction following transformation into the *E. coli* expression host N4830.

To express the *P. falciparum* CS protein gene from a full length clone lacking only the sequence encoding the putative 16 amino acid signal sequence, a StuI-RsaI DNA fragment was cloned directly into the StuI site of plasmid pPX1600. The sequence data of Dame et al. (1984, Science 225:593) was used to establish the CS protein reading frame within the restriction fragment and to predict the expression of the gene inserted into the StuI site of pPX1600. In this configuration, the full length mature gene is expressed from the P$_L$ promoter of the vector, and the initiating ATG (methionine) is that of the vector. The resulting plasmid was named pPX1534 and is diagrammed in FIG. 12.

7.8. CONSTRUCTION OF VECTORS WHICH EXPRESS LT-B/CS FUSION PROTEINS, BY INSERTION OF SYNTHETIC OLIGONUCLEOTIDE REPEAT SEQUENCES

To construct plasmid vectors which encode fusions of the *P. falciparum* or *P. berghei* immunodominant CS epitope to portions of the LT-B sequence, synthetic oligonucleotides encoding the epitope were ligated (following filling out of the recessed 3' ends) into the ClaI site of pPX100 (FIG. 4). The ClaI site was filled out by the action of Klenow enzyme in order to maintain the reading frame of the CS protein. In particular, the oligonucleotide designed to encompass the *P. falciparum* repeated epitope is shown below with the translated amino acid sequence below it:

```
5'... GAT  CCG  AAC  GCT  AAC  CCG  AAC  GCT  AAC  CCG  AAC  GCT
3'...      GGC  TTG  CGA  TTG  GGC  TTG  CGA  TTG  GGC  TTG  CGA
     Asp  Pro  [Asn Ala  Asn  Pro ][Asn Ala  Asn  Pro ][Asn Ala

AAC  CCG  AAC  GTT       ...3'
     TTG  GGC  TTG  CAA  CTA ...5'
     Asn  Pro ][Asn Val
```

This sequence includes three repeats of the consensus tetrapeptide [Asn-Ala-Asn-Pro]. This double-stranded oligonucleotide with sticky ends was blunted by Klenow enzyme and ligated into the ClaI site of pPX100 to yield plasmid pPX1532, in which two 48-mer oligonucleotide units were cloned in-frame with the first 30 amino acids of LT-B, followed by out-of-frame reading of 28 amino acids derived from the LT-B gene sequence. The recombinant clones were isolated and the plasmid DNA characterized in *E. coli* strain JM103.

7.9. EXPRESSION OF CIRCUMSPOROZOITE PROTEIN EPITOPES IN E. COLI AND IN SALMONELLA SSP.

Plasmids were designed as described supra to express variants of the circumsporozoite epitopes of either *P. falciparum* or *P. berghei*. As described therein, the expression of these proteins or portions of these proteins, was designed to be controlled by several different promoter systems known to function and drive gene expression in *E. coli*. As such, plasmid constructions were first isolated and tested in commonly available laboratory strains of *E. coli* such as JM103, which is a suitable strain for studying control of gene expression controlled by the lac promoter and repressor, and such as N99 (cI-) and N4830 (cI857), which are suitable *E. coli* hosts for examining gene expression controlled by the $P_L$ promoter. Because overexpression of gene products can often lead to deleterious effects on bacterial cell growth, control of gene expression can be important in obtaining the desired expression plasmid construction.

After desired plasmids were obtained in suitable *E. coli* hosts, plasmids carrying variants of the CS genes were transferred into several different species of Salmonella. Expressing plasmids were transferred into either *S. enteriditis* serotype dublin (commonly known as *S. dublin*) SL1438 (ATCC Accession No. 39184), *S. typhimurium* SL3261, or into *S. typhi* Ty523 or Ty541. (*Salmonella typhimurium* strain SL1479, ATCC Accession No. 39183, and *S. typhi* strain Ty531, ATCC Accession No. 39926, are other strains readily available for use.) The attenuated mouse virulent strains SL1438 and SL3261 carry a chromosomal deletion of the aroA gene (Hoiseth, S. K. and Stocker, B. A. D., 1981, Nature 291:238). The attenuated *S. typhi* strain Ty523 carries a chromosomal deletion of the aroA gene, and Ty541 carries an additional deletion of the purA gene. To test whether the chosen promoters function in each of the three host Salmonella strains, plasmids pPX1515, pPX1528, and pPX1601 were transformed into *S. typhimurium* LT-2, strain LB5010 (a non-restricting, transformable mutant), from which P22 phage lysates (Schmeiger, 1972, Mol. Gen. Genetics 119:75) were obtained to transduce each of the plasmids into the desired strain of Salmonella. Expression of the LT-B/CS fusion plasmids was examined in each of the bacterial cultures by the western technique of Section 6.10. As shown in FIG. 15, expression of the fusion protein controlled by each promoter was obtained in each of the host Salmonella strains. FIG. 15 shows that expression of the LT-B/CS fusion protein containing the *P. berghei* CS protein sequence, controlled by either the lac promoter, the tac promoter, or the lambda $P_L$ promoter, was observed in each of three attenuated Salmonella strains: SL3261, SL1438 and Ty523.

In addition, the expression of the *P. falciparum* CS protein repeat epitope fused to the first 30 amino acids of the mature LT-B protein was demonstrated (FIG. 16). Cell extracts of the Salmonella strains SL3261, SL1438, and Ty523, carrying pPX1532, were analyzed by isoelectric focussing as described in Section 6.10. The *P. falciparum* epitope was shown to be expressed in each of the strains, by binding anti-CS protein monoclonal antibodies as described in Section 6.10.

8. EXAMPLE: VACCINATION AGAINST MALARIA WITH ATTENUATED RECOMBINANT SALMONELLA WHICH EXPRESS CS PEPTIDES

As demonstrated in Section 7.9, the circumsporozoite proteins of either *P. falciparum* or *P. berghei* can be expressed at significant levels in several different Salmonella species including *S. dublin*, *S. typhi*, and *S. typhimurium*. The lac, tac, and $P_L$ promoters each is capable of driving the expression of LT-B/CS fusion proteins or portions of CS proteins. The immunodominant CS peptides encoded by synthetic oligonucleotides can be efficiently expressed when regulated by the $P_L$ promoter and translation initiation signals supplied by the expression vector. To test the vaccine potential of each of the plasmid constructs in an animal model system, each of the Salmonella bacteria carrying plasmids expressing CS peptides was used to vaccinate mice.

8.1. IMMUNOGENICITY IN MICE OF RECOMBINANT SALMONELLA WHICH EXPRESS CS PEPTIDES

The ability of recombinant Salmonella expressing CS peptides to elicit antibody against CS proteins was demonstrated by the detection of specific anti-CS antibodies in the sera of mice vaccinated with the recombinant bacteria. Six week old female C57B1/6 mice (Taconic labs) were used throughout this study. Log phase cultures of appropriate bacteria were washed three times in sterile phosphate-buffered saline (PBS), and resuspended to $10^8$ cells per ml in PBS. Mice were divided into groups of 5-10 and injected intraperitoneally (i.p.) with 0.1 ml of the appropriate bacterial cell suspension ($10^7$ cells) Alternatively, mice were inoculated orally with doses of $10^{10}$ recombinant bacteria on day 0, followed by a second dose of $10^{10}$ bacteria on day 3. Control groups received either Salmonella strains expressing LT-B proteins from recombinant plasmids, or Salmonella strains carrying pUC8 or pUC18 parental plasmids. Each mouse was bled before immunization, and sera was stored at $-70°$ C. for future analysis. Mice initially vaccinated by the i.p. route were bled again on week 4 and boosted with $10^8$ bacteria i.p. Mice which had been vaccinated orally were boosted on week 4 with $10^{10}$ bacteria, followed three days later with a second boosting dose. Serum samples were tested for the presence of anti-CS antibody and anti-LT-B antibody, by use of an enzyme-linked immunoabsorbent assay (ELISA), as described in Section 6.12.

The actual OD (optical density) values of control and experimental sera at 1:160 dilution are presented in FIG. 17. Titers were determined based on a cutoff OD corresponding to the mean OD of pre-immune sera plus 3 standard deviations. A four fold rise in titer from pre- to post-immune sera was considered significant. *Salmonella dublin* SL1438 carrying pPX1528 or pPX1601 plasmids induced significant anti-CS primary antibody response but no anti-LT-B antibody response; both plasmids express an LT-B/CS fusion protein. In contrast, pPX1527 in SL1438 (expressing the LT-B gene) stimulated anti-LT-B antibodies. A slightly higher anti-CS response was observed with pPX1601 in SL1438 (expressing the CS gene under the control of the $P_L$ promoter) than that with pPX1528 in SL1438 (expressing the CS gene under the control of the tac promoter), suggesting that a higher level of expression may be very critical to elicit greater antibody response in this system.

Boostable response was observed for each of the plasmid constructions, with the highest titer being observed with the bacteria expressing the largest amount of CS protein or LT-B/CS fusion protein. Mice that had been vaccinated with *Salmonella dublin* SL1438 expressing LT-B/CS fusion protein driven by the lac promoter showed no significant response after either primary or secondary vaccination, suggesting that the expression level of the fusion protein was too low.

8.2. PROTECTION AGAINST PLASMODIUM INFECTION IN MICE AFTER IMMUNIZATION WITH RECOMBINANT SALMONELLA EXPRESSING CS PEPTIDES

The efficacy of the recombinant Salmonella strains expressing CS proteins for use as vaccines was demonstrated in the mouse model system, by showing protection against Plasmodium infection in immunized mice upon sporozoite challenge. Although expression of the *P. falciparum* immunodominant epitope can be demonstrated in *S. typhi* and other Salmonella, mice cannot be infected with sporozoites of *P. falciparum*. To demonstrate the ability of recombinant *Salmonella dublin* SL1438 carrying LT-B/CS fusion protein-encoding plasmids or CS protein-encoding plasmids to elicit protection, mice previously vaccinated with recombinant Salmonella were challenged with either a low dose (1000/mouse) or a high dose ($10^4$/mouse) of *P. berghei* sporozoites, by tail vein injection. As a control, unvaccinated mice were also challenged.

*S. dublin* SL1438, carrying either plasmids pPX1528 (tac-promoted) or pPX1601 ($P_L$-promoted) expressing the LT-B/CS fusion protein, or carrying pPX1529 expressing the immunodominant repeat region of the CS protein, are capable of eliciting a protective response. In control experiments, vaccination at week zero and boosting at week four with either 10 micrograms D-16-N-KLH (DPAPPNAN-KLH; Egan et al., 1987, Science 236:453) or with 10 micrograms of partially purified LT-B/CS fusion protein derived from *E. coli* (strain N4830 containing pPX1601) elicits no protection. Although significant titers of anti-CS antibody are observed in these control groups, little protection against sporozoite challenge is seen.

Mice orally inoculated with $10^9$ *S. dublin* (carrying pPX1601) or *S. dublin* control cells and boosted after 4 weeks with $10^{10}$ of those same organisms, were challenged at week 13. Eight days after challenge with $10^3$ *P. berghei* sporozoites by tail vein injection, 4 out of 5 of the animals immunized with the control *S. dublin* cells exhibited patent blood stage parasitemia, whereas only 1 out of 5 of the animals immunized with *S. dublin* (carrying pPX1601) showed blood-stage parasites. Thus, 20% of the control animals escaped infection, whereas 80% of the immunized animals were protected.

Thus, attenuated live Salmonella are capable of delivering a sporozoite epitope to the immune system in such a manner as to elicit protective immunity not achieved by customary routs of vaccination.

9. DEPOSIT OF MICROORGANISMS

The following bacterial strains, carrying the listed plasmids encoding a Plasmodium epitope, have been deposited with the American Type Culture Collection (ATCC), Rockville, Md., and have been assigned the indicated accession numbers:

| Bacterial Strain | Plasmid | Accession Number |
|---|---|---|
| *Salmonella typhi* Ty523 | pPX1532: A plasmid which expresses a fusion protein of the first thirty amino acids of LT-B followed by a dimer of four tetrapeptide repeats, each of the *P. falciparum* CS protein, fused to 28 amino acids read out-of-frame from the LT-B gene. This fusion protein is expressed from the lac promoter. | 67519 |
| *Salmonella enteritidis* serotype dublin SL1438 | pPX1528: A plasmid which expresses a fusion protein of the first thirty amino acids of LT-B at the amino-terminus followed by 223 amino acids of the *P. berghei* CS protein transcribed from the XmnI fragment of the CS protein gene, with 28 amino acids read out-of-frame from the LT-B gene at the carboxy-terminus. This fusion protein is expressed from the tac promoter. | 67521 |
| *Salmonella enteritidis* serotype dublin SL1438 | pPX1601: A plasmid which expresses a fusion protein of the first thirty amino acids of LT-B at the amino-terminus followed by 223 amino acids of the *P. berghei* CS protein transcribed from the XmnI fragment of the CS protein gene, with 28 amino acids read out-of-frame from the LT-B gene at the carboxy-terminus. This fusion protein is expressed from the $P_L$ promoter. | 67520 |
| *E. coli* N99cI⁻ | pPX1534: A plasmid which expresses the full-length *P. falciparum* CS protein gene (lacking only the sequence encoding the putative 16 amino acid signal sequence). This protein is expressed from the $P_L$ promoter. | 67518 |

The present invention is not to be limited in scope by the microorganisms deposited since the deposited embodiment is intended as a single illustration of one aspect of the invention and any microorganisms which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides are approximate and are used for purposes of description, and figures which diagrammatically depict DNA sequences are not necessarily drawn to scale.

What is claimed is:

1. An attenuated enteroinvasive bacterium of the genus Salmonella or Shigella comprising a recombinant DNA sequence which encodes an epitope of the circumsporozoite protein of a malaria parasite.

2. The recombinant bacterium of claim 1 wherein the bacterium is *Salmonella typhi, Salmonella typhimurium* or *Salmonella enteritidis*.

3. The bacterium of claim 2 which is selected from the group consisting of Ty21, Ty21a, Ty523 and Ty541.

4. The recombinant bacterium of claim 2 wherein the bacterium is a serotype dublin.

5. The bacterium of claim 1 wherein the epitope of the repeat region of the circumsporozoite protein.

6. The bacterium of claim 1 wherein the epitope is Region I or Region II of the circumsporozoite protein.

7. The bacterium of claim 1 wherein the recombinant DNA sequence encodes a fusion protein comprising an epitope of the circumsporozoite protein and the B-subunit of the heat-labile enterotoxin of *E. coli* or a portion thereof, such that said fusion protein is immunogenic.

8. The bacterium of claim 1 wherein the DNA sequence is expressed under the control of the lac operon promoter of *E. coli*, the tac promoter, the leftward promoter of bacteriophage lambda, or the rightward promoter of bacteriophage lambda.

9. The bacterium of claim 1 or 2 wherein the malaria parasite is *Plasmodium falciparum*.

10. The bacterium of claim 9 wherein the epitope comprises the amino acid sequence asn-ala-asn-pro.

11. The bacterium of claim 1 wherein the bacterium is *Salmonella typhi* ATCC accession number 67519.

12. The bacterium of claim 1 wherein the malaria parasite is *Plasmodium vivax*.

13. The bacterium of claim 1 wherein the malaria parasite is *Plasmodium ovale*.

14. The bacterium of claim 1 wherein the malaria parasite is *Plasmodium malariae*.

15. The bacterium of claim 1 wherein the malaria parasite is *Plasmodium berghei*.

16. The bacterium of claim 15 wherein the epitope comprises the amino acid sequence asp-pro-ala-pro-pro-asn-ala-asn.

17. The bacterium of claim 1 wherein the bacterium is *Salmonella enteriditis* ATCC accession number 67521.

18. The bacterium of claim 1 wherein the bacterium is *Salmonella enteritidis* ATCC accession number 67520.

19. The bacterium of claim 1 wherein the malaria parasite is *Plasmodium yoelii*.

20. The bacterium of claim 1 wherein the malaria parasite is *Plasmodium knowlesi*.

21. The bacterium of claim 1 wherein the malaria parasite is *Plasmodium cynomolgi*.

22. A method of expressing an epitope of the circumsporozoite protein of a malaria parasite comprising:
   a. transforming an attenuated enteroinvasive bacterium of the genus Salmonella or Shigella with a vector comprising a recombinant DNA sequence which encodes an epitope of the circumsporozoite protein of a malaria parasite; and
   b. allowing the bacterium to grow under conditions which induce the expression of said circumsporozoite protein.

23. The method of according to claim 22 wherein the bacterium is Salmonella.

24. The method according to claim 23 wherein the bacterium is *Salmonella typhi, Salmonella typhimurium* or *Salmonella enteritidis*.

25. The method according to claim 22 wherein the DNA sequence is expressed under the control of the lac operon promoter of *E. coli*.

26. The method according to claim 23 wherein the DNA sequence is expressed under the control of the lac operon promoter of *E. coli*.

27. The method according to claim 26 wherein the bacterium is *Salmonella typhi* ATCC accession number 67519.

28. The method according to claim 22 wherein the DNA sequence is expressed under the control of the tac promoter.

29. The method according to claim 23 wherein the DNA sequence is expressed under the control of the tac promoter.

30. The method according to claim 29 wherein the bacterium is *Salmonella enteritidis* ATCC accession number 67521.

31. The method according to claim 22 wherein the DNA sequence is expressed under the control of the leftward promoter of bacteriophage lambda.

32. The method according to claim 23 wherein the DNA sequence is expressed under the control of the leftward promoter of bacteriophage lambda.

33. The method according to claim 32 wherein the bacterium is *Salmonella enteritidis* ATCC accession number 67520.

34. The method according to claim 22 or 23 wherein the DNA sequence is expressed under the control of the rightward promoter of bacteriophage lambda.

35. The method according to claim 22 or 23 wherein the malaria parasite is *Plasmodium falciparum*.

36. The method according to claim 22 wherein the malaria parasite is *Plasmodium vivax*.

37. The method according to claim 22 wherein the malaria parasite is *Plasmodium ovale*.

38. The method according to claim 22 wherein the malaria parasite is *Plasmodium malariae*.

39. The method according to claim 22 or 23 wherein the malaria parasite is *Plasmodium berghei*.

40. The method according to claim 22 wherein the malaria parasite is *Plasmodium yoelii*.

41. The method according to claim 22 wherein the malaria parasite is *Plasmodium knowlesi*.

42. The method according to claim 22 wherein the malaria parasite is *Plasmodium cynomolgi*.

43. An attenuated enteroinvasive bacterium of the genus Salmonella or Shigella having an arcA or galE mutation and comprising a recombinant DNA sequence which encodes an epitope of the circumsporozoite protein of a malaria parasite.

44. The attenuated bacterium of claim 43, wherein the circumsporozoite protein is derived from *Plasmodium falciparum*.

45. The attenuated bacterium of claim 43, wherein the malaria parasite is *Plasmodium berghei*.

46. The attenuated bacterium of claim 43, wherein the recombinant DNA sequence encodes a fusion protein comprising an epitope of the circumsporozoite protein and the B-subunit of heat-labile enterotoxin of *E. coli* or a portion thereof, such that said fusion protein is immunogenic.

47. The attenuated bacterium of claim 46, wherein the fusion protein comprises the N-terminal 30 amino acids of the B subunit of the heat-labile enterotoxin of *E. coli*.

48. The attenuated bacterium of claim 46, wherein the bacterium is *Salmonella typhi, Salmonella typhimurium, Salmonella dublin* or *Salmonella enteritidis*.

49. The attenuated bacterium of claim 46, wherein the malaria parasite is *Plasmodium falciparum* or *Plasmodium vivax*.

50. The attenuated bacterium of claim 46, wherein the malaria parasite is *Plasmodium ovale, Plasmodium malariae, Plasmodium berghei, Plasmodium yoelii, Plasmodium knowlesi* or *Plasmodium cynomolgi*.

* * * * *

UNITED STATES PATENT AND TRADEMARK OFFICE
CERTIFICATE OF CORRECTION

PATENT NO.   : 5,112,749
DATED        : May 12, 1992
INVENTOR(S)  : Brey, III et al.

It is certified that error appears in the above-identified patent and that said Letters Patent is hereby corrected as shown below:

Column 41, Claim 5, line 5, delete "of" (2nd occ.) and insert ---is---.

Column 42, Claim 43, line 41, delete "arcA" and insert ---aroA---.

Signed and Sealed this

Seventh Day of September, 1993

Attest:

BRUCE LEHMAN

Attesting Officer    Commissioner of Patents and Trademarks